United States Patent
Gaffield

(10) Patent No.: US 12,411,978 B2
(45) Date of Patent: Sep. 9, 2025

(54) CHARTING LOGIC DECISION SUPPORT IN ELECTRONIC PATIENT CHARTING

(71) Applicant: ZOLL Medical Corporation, Chelmsford, MA (US)

(72) Inventor: David Gaffield, Broomfield, CO (US)

(73) Assignee: ZOLL Medical Corporation, Chelmsford, MA (US)

( * ) Notice: Subject to any disclaimer, the term of this patent is extended or adjusted under 35 U.S.C. 154(b) by 355 days.

(21) Appl. No.: 17/452,830

(22) Filed: Oct. 29, 2021

(65) Prior Publication Data

US 2022/0164473 A1    May 26, 2022

Related U.S. Application Data

(63) Continuation of application No. 15/467,194, filed on Mar. 23, 2017, now abandoned.

(60) Provisional application No. 62/315,832, filed on Mar. 31, 2016.

(51) Int. Cl.
*G06F 21/62* (2013.01)
*G16H 10/60* (2018.01)

(52) U.S. Cl.
CPC ......... *G06F 21/6245* (2013.01); *G16H 10/60* (2018.01)

(58) Field of Classification Search
CPC .... G06F 21/6245; G16H 10/60; G16H 40/67; G16Z 99/00
See application file for complete search history.

(56) References Cited

U.S. PATENT DOCUMENTS

| | | | |
|---|---|---|---|
| 6,747,561 B1 * | 6/2004 | Reeves | G06F 1/1656 340/573.5 |
| 8,169,315 B2 | 5/2012 | Smith et al. | |
| 8,554,170 B2 | 10/2013 | Franz et al. | |
| 8,712,793 B2 | 4/2014 | Jones et al. | |
| 9,729,480 B2 | 8/2017 | Bell | |
| 10,574,606 B2 | 2/2020 | Bell | |

(Continued)

FOREIGN PATENT DOCUMENTS

| | | | | |
|---|---|---|---|---|
| JP | 2002032475 A | * | 1/2002 | G06Q 10/10 |
| JP | 4393112 B2 | * | 1/2010 | |

(Continued)

OTHER PUBLICATIONS

Wikipedia."HealthLevel7". RetrievedfromtheWaybackMachineasof Nov. 13, 2008.Accessed Dec. 9, 2019. (Year: 2008).*

(Continued)

*Primary Examiner* — Lynda Jasmin
*Assistant Examiner* — Shaun D Sensenig
(74) *Attorney, Agent, or Firm* — Finch & Maloney PLLC

(57) ABSTRACT

Techniques for charting a medical event are disclosed. In one embodiment, the techniques may be realized as a system for charting a medical event, comprising a processor communicably coupled to a database and to a patient charting system. The processor may be configured to during the medical event: receive charting data from the patient charting system; query the database with the charting data to obtain additional data that is associated with at least some of the charting data; and send the additional data to the patient charting system to populate a patient chart during the medical event.

25 Claims, 14 Drawing Sheets

(56) References Cited

U.S. PATENT DOCUMENTS

| | | | |
|---|---|---|---|
| 2003/0052788 A1* | 3/2003 | Kwong-Tai Chung | H01Q 21/28 235/487 |
| 2003/0105649 A1 | 6/2003 | Sheiner et al. | |
| 2003/0195567 A1 | 10/2003 | Jayne et al. | |
| 2005/0240613 A1* | 10/2005 | Logan, Jr. | G06Q 50/22 707/999.102 |
| 2006/0229909 A1 | 10/2006 | Kaila et al. | |
| 2007/0083392 A1* | 4/2007 | Zaleski | G16H 20/10 705/2 |
| 2008/0133572 A1* | 6/2008 | Verhey-Henke | G16H 10/20 707/999.102 |
| 2009/0037225 A1* | 2/2009 | Burchianti, II | G16H 40/20 705/7.18 |
| 2010/0227585 A1 | 9/2010 | Carroll et al. | |
| 2011/0119088 A1 | 5/2011 | Gunn | |
| 2011/0295078 A1* | 12/2011 | Reid | G16H 40/67 600/300 |
| 2012/0158074 A1 | 6/2012 | Hall | |
| 2012/0191476 A1* | 7/2012 | Reid | G16H 10/65 705/3 |
| 2013/0096649 A1* | 4/2013 | Martin | G16H 40/67 607/60 |
| 2013/0275151 A1 | 10/2013 | Moore et al. | |
| 2014/0019159 A1 | 1/2014 | Singh et al. | |
| 2014/0046940 A1 | 2/2014 | Thomson et al. | |
| 2014/0249854 A1* | 9/2014 | Moore | G16H 10/60 705/3 |
| 2014/0337047 A1 | 11/2014 | Mears et al. | |
| 2014/0365241 A1 | 12/2014 | Dillie et al. | |
| 2015/0120794 A1* | 4/2015 | Phelan | G06F 16/173 707/828 |
| 2015/0127379 A1 | 5/2015 | Sorenson | |
| 2015/0242574 A1 | 8/2015 | Antony et al. | |
| 2016/0070864 A1* | 3/2016 | Dotan | G16H 40/67 705/3 |
| 2016/0162643 A1* | 6/2016 | Newbold | G16H 10/65 705/3 |
| 2016/0180044 A1* | 6/2016 | Delisle | G16H 40/63 705/3 |
| 2017/0296107 A1 | 10/2017 | Reid et al. | |
| 2019/0214115 A1 | 7/2019 | Bell | |

FOREIGN PATENT DOCUMENTS

| | | | | |
|---|---|---|---|---|
| WO | 2014144846 A1 | 9/2014 | | |
| WO | 2015066650 A1 | 5/2015 | | |
| WO | WO-2015191873 A1 * | 12/2015 | | G16H 10/60 |

OTHER PUBLICATIONS

Lupşe et al. Using HL7 CDA and CCD standards to improve communication between healthcare information systems. 2011 IEEE 9th International Symposium on Intelligent Systems and Informatics. Sep. 8-10, 2011. May 29, 2025. <https://ieeexplore.ieee.org/stamp/stamp.jsp?tp=&arnumber=6034371> (Year: 2011).*

ZOLL Data Systems, RescueNet Billing—Dispatch Release Notes, Software Version 4.6.1, Dec. 8, 2015, 5 pages.

ZOLL Data Systems, "RescueNet Billing User's Guide," Software Version 4.6, 2015, 450 pages.

ZOLL Data Systems, "RescueNet Dispatch—Billing 4.6 Services Install Guide," Oct. 23, 2015, 34 pages.

ZOLL Data Systems, RescueNet Dispatch—Billing Administration Guide, Release 4.6.1, Oct. 22, 2015, 740 pages.

ZOLL Data Systems, "RescueNet Dispatch—Billing Upgrade Guide for Administrators," Oct. 21, 2015, 16 pages.

ZOLL Data Systems, RescueNet Eligibility Services Installation Guide, Software Release 4.6, 2015, 7 pages.

ZOLL Data Systems, "RescueNet ePCR 5.4.3 Defect Release Notes," Jan. 26, 2014, 1 page.

ZOLL Data Systems, "RescueNet ePCR 5.4.3 Feature Release Notes," Jan. 26, 2014, 1 page.

ZOLL Data Systems, "RescueNet ePCR Suite Administrator Guide," Software Version 5.4.3, 2015, 389 pages.

ZOLL Data Systems, RescueNet TabletPCR and WebPCR User Guide, Software Version 5.4.3, 2015, 205 pages.

Smiley et al., "Implementation of EMS Access to Patient History" https://www.jems.com/operations/orange-county-calif-begins-field-implementation-of-ems-access-to-patient-history-via-hie/ May 1, 2017 (9 pages).

RemoteOperations, SecureFlow Pro HL7 Specification ADS, MDM and ACK Message Types, Document Version 1.2, updated Nov. 3, 2005 (21 pages).

Kno2, Image Trend Enable Broad-based Interoperability for EMS, Oct. 16, 2019 (7 pages).

www.imagetrend.com, Website known to have been captured as early as Jul. 25, 2002 (3 pages).

www.imagetrend.com/ems/, Website know to have been captured as early as Nov. 19, 2002 (33 pages).

ZOLL Data Systems, EMS and Hospital Partners: Transform the Way You Collaborate with ZOLL Care Exchange, Copyright 2021 (8 pages).

\* cited by examiner

CHARTING LOGIC DECISION SUPPORT IN ELECTRONIC PATIENT CHARTING

CROSS-REFERENCE TO RELATED APPLICATIONS

This application is a continuation of U.S. patent application Ser. No. 15/467,194 (filed 23 Mar. 2017), which claims the benefit of U.S. Provisional Patent Application 62/315,832 (filed 31 Mar. 2016). Both of these priority applications are incorporated by reference herein in their entirety for all purposes.

TECHNICAL FIELD

Embodiments of the present disclosure relate generally to electronic patient charting, and more particularly, to methods and systems for facilitating efficient and streamlined electronic patient charting during a medical event, as well as enabling third parties to access patent charting data during the medical event.

BACKGROUND

It is often desirable to be able to have complete and accurate patient information during a medical event. Such complete and accurate patient information enables medical personnel to diagnose a patient quickly and accurately, provide treatment if necessary, and avoid errors. For example, in response to a 911 call, based on the patient's medical history of cardiovascular disease, a medical personnel may quickly diagnose the patient as having a heart attack and provide an appropriate treatment.

However, complete and accurate patient information may not be available. During a medical event, for example, after medical personnel arrive to take the patient into an ambulance, even if the patient is able to provide biographical information such as name and age, the patient may not be able to accurately describe the patient's medical history and the medications that the patient is taking.

In addition, entering patient charting information may be time-consuming and error-prone. Some state regulations require certain information to be provided for an emergency medical event. If a medical personnel has to spend time to enter patient charting information, the time to treat the patient may be lessened. In situations, such as emergency medical events, where users are pressed for time, patient charting information entry by a clinical user (e.g., emergency medical care personnel) can be prone to inadvertent mistakes. Patient information may also be required for medical devices, for example, a defibrillator. Entering patient information into a medical device may also take up medical personnel time.

Further, patient charting information may not be available to third parties, such as patient family members and healthcare providers in a hospital to which the patient is being taken. The lack of access to patient charting information may hinder efficient treatment when the patient arrives at the hospital. It may also prevent patient family members from locating the patient or receiving information about the patient's condition.

SUMMARY

Techniques for charting a medical event are disclosed. In one embodiment, the techniques may be realized as a system for charting a medical event, comprising a processor communicably coupled to a database and to a patient charting system. The processor may be configured to during the medical event: receive charting data from the patient charting system; query the database with the charting data to obtain additional data that is associated with at least some of the charting data; and send the additional data to the patient charting system to populate a patient chart during the medical event.

In accordance with other aspects of this embodiment, the charting data may comprise a name and an address of a patient associated with the medical event.

In accordance with other aspects of this embodiment, the charting data may comprise a name, a birth date and a gender of a patient associated with the medical event.

In accordance with other aspects of this embodiment, the charting data may comprise a driver license number of a patient associated with the medical event.

In accordance with other aspects of this embodiment, the charting data may comprise an assessment of a patient associated with the medical event.

In accordance with other aspects of this embodiment, the additional data may comprise previous recorded physiological data of a patient associated with the medical event.

In accordance with other aspects of this embodiment, the physiological data may comprises medication allergies.

In accordance with other aspects of this embodiment, the charting data may comprise a patient identifier.

In still another embodiment, the techniques may be realized as a system for charting a medical event, comprising a processor communicably coupled to a database and to a patient charting system. The processor may be configured to, during the medical event: receive charting data from the patient charting system, the charting data having been entered into the patient charting system about the patient during the medical event; query the database with the charting data to obtain additional data that is associated with at least some of the charting data, wherein the additional data includes data of a non-clinical type; and send at least one of the charting data and the additional data to a clinical device while the clinical device is being used to treat the patient during the medical event.

In accordance with other aspects of this embodiment, the clinical device may be a defibrillator.

In accordance with other aspects of this embodiment, the clinical device may be a wearable defibrillator.

In accordance with other aspects of this embodiment, the clinical device may be a cardiopulmonary resuscitation monitoring and assistance device.

In accordance with other aspects of this embodiment, the charting data may include an identification of a patient, and the additional data may comprise identification information of the clinical device that is treating the patient.

In accordance with other aspects of this embodiment, the charting data may include a location of the patient being treated by the clinical device, and the additional data may comprise identification information of the clinical device that is at the location.

In accordance with other aspects of this embodiment, the additional data may comprise physiological data of the patient.

In accordance with other aspects of this embodiment, the additional data may comprise physiological data of the patient and the clinical device may be configured to adjust an operational parameter of the clinical device based on the additional data.

In accordance with other aspects of this embodiment, the additional data may comprise a patient medical history and the clinical device may be configured to adjust an operational parameter of the clinical device based on the additional data.

In accordance with other aspects of this embodiment, the additional data may comprise at least one of an age, a gender, a weight of the patient and the clinical device may be configured to adjust an operational parameter of the clinical device based on the additional data.

In still another embodiment, the techniques may be realized as a system for charting a medical event, comprising: a processor communicably coupled to a database and to a third party interface system. The processor may be configured to, during the medical event: receive patient charting data via input by a clinical user; permit the clinical user to selectively view all or some of the patient charting data; receive input from a third party user via the third party interface system; authenticate the third party user via the input; and once authenticated, permit the third party user to selectively view all or some of the patient charting data with the third party interface system in at least the same manner as the processor permits the clinical user to selectively view all or some of the patient charting data.

In accordance with other aspects of this embodiment, the third party user may comprise at least one of a patient, a patient family member, an emergency medical service personnel, and a healthcare provider.

In accordance with other aspects of this embodiment, the processor may be further configured to alert the patient family member of a destination healthcare facility for a transport of the patient.

In accordance with other aspects of this embodiment, the processor may be further configured to permit the third party user to view the patient charting data as the clinical user inputs the patient charting data.

In accordance with other aspects of this embodiment, the processor may be further configured to permit the third party user to view the patient charting data only if the third party's access to the patient charting data is compliant with HIPAA regulations.

In accordance with other aspects of this embodiment, the processor may be further configured to permit the third party user to view the patient charting data only if the third party is identified by the patient on a medical record release form previously signed by the patient.

In accordance with other aspects of this embodiment, the processor may be further configured to authenticate the third party user based on at least one of identification information, a code, or a badge associated with the third party user.

In still another embodiment, the techniques may be realized as a system for charting a medical event, comprising: a patient charting system communicably coupled to a database. The patient charting system may be configured to, during the medical event: receive charting data via input by a user; query the database with the charting data to obtain additional data that is associated with at least a portion of the charting data, wherein the additional data includes data of a non-physiological type; receive the additional data with the patient charting system; and customize a template according to which the patient charting system prompts the user for entry of the charting data based on at least one of the charting data and the additional data.

In accordance with other aspects of this embodiment, the patient charting system may be configured to disable one or more entries of the template in response to the charting data.

In accordance with other aspects of this embodiment, when the received charting data indicates cancellation of the medical event, the patient charting system may be configured to customize the template by disabling patient-related entries of the template.

In accordance with other aspects of this embodiment, the patient charting system may be configured to customize the template by disabling entries related to pregnancy based on at least one of patient gender and patient age in the charting data.

In accordance with other aspects of this embodiment, the additional data may include only data of the non-physiological type.

In accordance with other aspects of this embodiment, the patient charting system may be configured to validate the input by the user based on valid ranges of the input.

In accordance with other aspects of this embodiment, the patient charting system may be configured to validate the input by the user and prompt the user to correct errors before completing data entry.

In accordance with other aspects of this embodiment, when the received charting data indicates a data value outside of a range, the patient charting system may be configured to customize the template by visually alerting the user with the template that the data value is outside of the range.

In accordance with other aspects of this embodiment, the patient charting system may be further configured to prompt the user to re-enter the data value.

In accordance with other aspects of this embodiment, when the received charting data indicates a single patient, the patient charting system may be configured to customize the template by disabling entries of the template that relate to multiple patients.

BRIEF DESCRIPTION OF THE DRAWINGS

FIG. 11 illustrates an exemplary graphical user interface for the patient charting system where charting data indicates a type of service requested, according to some embodiments.

FIG. 13 illustrates an exemplary graphical user interface for the patient charting system where charting data indicates patient signature, according to some embodiments.

Figure 1:
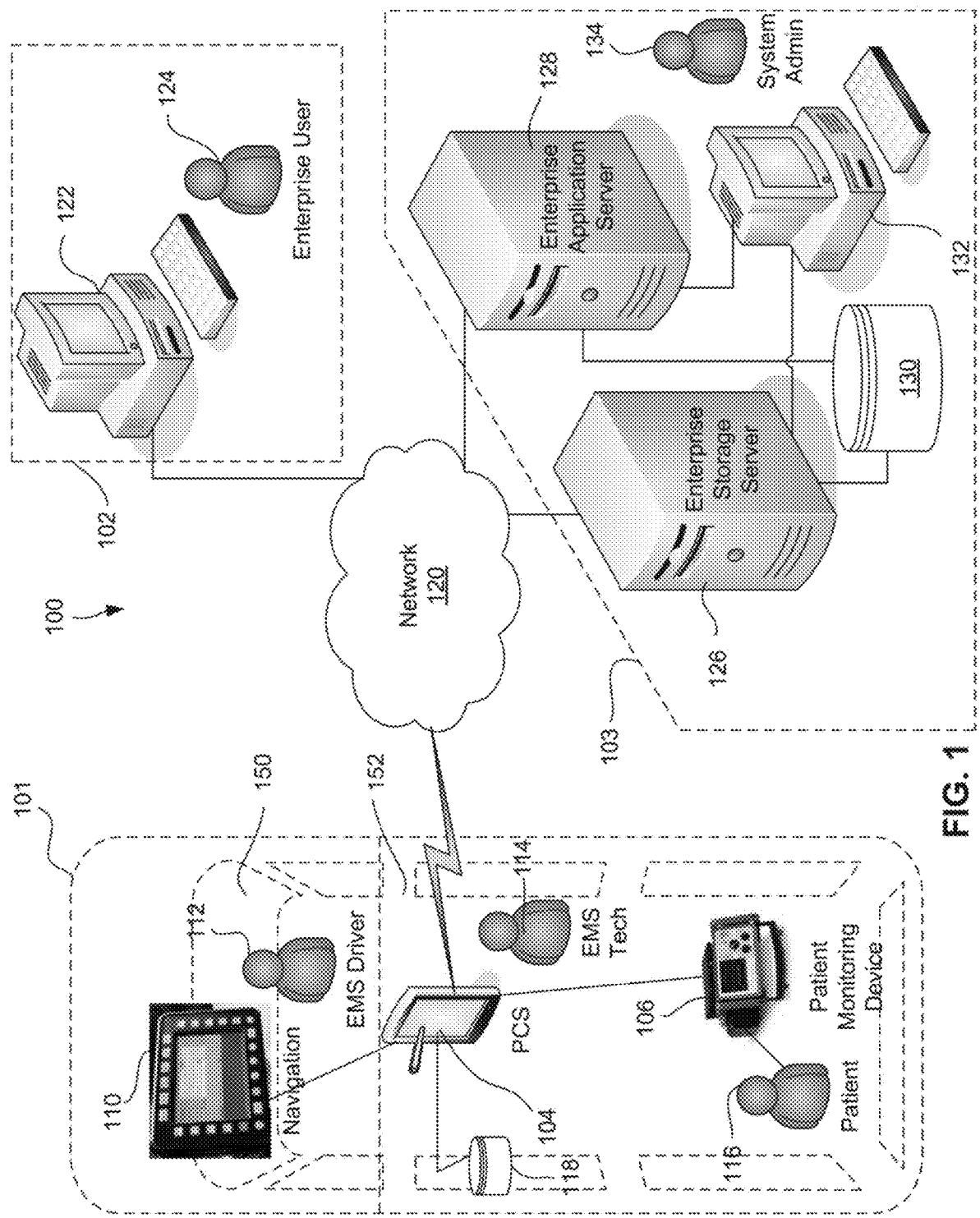
FIG. 1 illustrates a system for mobile and enterprise real-time display of medical information collected from multiple different EMS devices, according to some embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Complete and accurate patient information, including patient biographical information, medical condition, medications, allergies, and the like can impact accurate diagnosis and treatment. Complete and accurate patient information may also save precious time for medical personnel, such that they may have more time to treat the patient, rather than spending time to enter patient charting information. Complete and accurate patient information may also be provided to third parties such as care providers in a hospital to enable efficient and accurate treatment and patient family members to locate the whereabouts and/or to observe the condition of the patient.

For example, consider an illustrative scenario of a crew of emergency medical services (EMS) caregivers in an ambulance being called upon to pick up and treat a patient suffering from an emergency medical condition (e.g., a heart attack, or a traumatic injury), and to deliver the patient to a treating hospital. During the course of the emergency encounter, the EMS caregivers need to enter patient charting information. This patient charting information may comprise information regarding the patient, such as observed patient symptoms during the encounter, observed patient physiological parameters (such as heart rate, ECG traces, temperature, blood-oxygen data, and the like), and treatments or medications administered during the encounter. The patient charting information may include information, such as any known allergies to medication, relevant medical history, and/or additional patient medical conditions. This patient charting information may also comprise information regarding the emergency medical event, such as type of service requested, response mode, and triage classification.

It may be desirable that at least some of the patient charting information is automatically populated based on what has been entered. For example, if the patient social security number has been entered, it may be desirable that relevant additional patient information such as patient name, gender, age, allergies, medical conditions, medications will be automatically entered into corresponding entry fields. If the relevant additional patient information indicates that the patient is allergic to acetaminophen, then the EMS caregiver can avoid treating the patient with acetaminophen as a pain-reliever, avoiding potential medical errors. A notification relating to such information, and/or other additional patient information, may be sent to the caregiver in the form of an alert and/or alarm, for example a visual and/or audio and/or other type of alert or alarm. As another example, if the patient is treated by a medical device, such as a defibrillator, it may be desirable that patient charting information is sent to the medical device. Third party access to patient charting information and customized data entry template may also be desirable.

Some embodiments of the present disclosure include systems, apparatus, and methods for charting a medical event. In some cases, additional data that is associated with the received charting data may be obtained. The additional data may be used to populate a patient chart. The additional data may be obtained during the medical event, in time to facilitate treating physician (e.g., emergency medical personnel) clinical decision making to diagnose and/or treat a patient more accurately.

Other embodiments of the present disclosure include systems, apparatus, and methods for charting a medical event. Additional data that is associated with charting data may be obtained. The charting data may have already been entered by, for example, a treating physician or a nurse or an emergency medical service personnel. The charting data and/or the additional data may be sent to a clinical device. In some cases, the charting data and/or the additional data sent to the clinical device relieves the need of manual patient information entry to the clinical device. In some cases, the charting data and/or the additional data facilitates the clinical decision and/or adjusts at least an operational parameter of the clinical device.

Yet other embodiments of the present disclosure include systems, apparatus, and methods for charting a medical event. In some cases, third parties are able to access and view the patient charting data. Third parties may be able to access and view the patient charting data in the same manner as the clinical user. For example, third parties may be able to view the patient charting data as the data is entered by the clinical user. If there is an alert that the clinical user sees, the third parties may see it as well.

Yet other embodiments of the present disclosure include systems, apparatus, and methods for charting a medical event. In some cases, certain data entries are greyed out or otherwise deactivated in response to user's data entry in one entry. These data entries no longer need to be filled out. In some cases, based on the additional data received, a user of the patient charting system is alerted.

As illustrated in FIG. 1, a system 100 according to embodiments of the present disclosure performs advanced data management, integration and presentation of EMS data from multiple different devices. System 100 includes a mobile environment 101, an enterprise environment 102, and an administration environment 103. Devices within the various environments 101, 102, 103 may be communicably coupled via a network 120, such as, for example, the Internet.

As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network, or direct coupling.

According to embodiments of the present disclosure, the mobile environment 101 is an ambulance or other EMS vehicle—for example a vehicular mobile environment (VME). The mobile environment may also be the local network of data entry devices as well as diagnostic and therapeutic devices established at time of treatment of a patient or patients in the field environment, such as an "At Scene Patient Mobile Environment" (ASPME). The mobile environment may also be a combination of one or more of VMEs and/or ASPMEs. The mobile environment may include a navigation device 110 used by the driver 112 to track the mobile environment's position 101, locate the mobile environment 101 and/or the emergency location, and locate the transport destination, according to embodiments of the present disclosure. The navigation device 110 may include a Global Positioning System ("GPS"), for example. The navigation device 110 may also be configured to perform calculations about vehicle speed, the travel time between locations, and estimated times of arrival. According to embodiments of the present disclosure, the navigation device 110 is located at the front of the ambulance to assist the driver 112 in navigating the vehicle. The navigation device 110 may be, for example, a RescueNet® Navigator onboard electronic data communication system available from ZOLL® Data Systems of Broomfield, Colorado.

As illustrated in FIG. 1, a patient monitoring device 106 and a patient charting system (PCS) 104 are also often used for patient care in the mobile environment 101, according to embodiments of the present disclosure. The EMS technician 114 attaches the patient monitoring device 106 to the patient 116 to monitor the patient 116. The patient monitoring device 106 may be, for example, a defibrillator device with electrodes and/or sensors configured for attachment to the patient 116 to monitor heart rate and/or to generate electrocardiographs ("ECG's"), according to embodiments of the present disclosure. The patient monitoring device 106 may also include sensors to detect or a processor to derive or calculate other patient conditions. For example, the patient monitoring device 106 may monitor, detect, treat and/or derive or calculate blood pressure, temperature, respiration rate, blood oxygen level, end-tidal carbon dioxide level, pulmonary function, blood glucose level, and/or weight, according to embodiments of the present disclosure. The patient monitoring device 106 may be a ZOLL® E-Series®, X-Series®, R-Series®, or other defibrillator available from ZOLL® Medical Corporation of Chelmsford, Massachusetts, according to embodiments of the present disclosure. A patient monitoring device may also be a patient treatment device, or another kind of device that includes patient monitoring and/or patient treatment capabilities, according to embodiments of the present disclosure. For example, if the patient monitoring device is a defibrillator, the patient monitoring device can also deliver therapeutic electric shocks to the patient. In other embodiments, the patient monitoring device can also deliver other types of treatments, such as operating a respirator, or administering drugs or other medication.

The PCS 104 can be a device used by the EMS technician 114 to generate records and/or notes about the patient's 116 condition and/or treatments applied to the patient, according to embodiments of the present disclosure. PCS 104 can be a device, PCS 104 can be a cloud-implemented software interface running on a processor or device, and/or PCS 104 can be a combination thereof, according to some embodiments. PCS 104 may include a combination of devices, according to some embodiments. PCS 104 may receive and/or send data from and/or to other devices like patient monitoring device 106, in one embodiment. In another embodiment, PCS 104 may communicate with another device or system which aggregates or otherwise receives data from other devices, such as patient monitoring device 106. For example, a patient charting device may be utilized to access a patient charting system as described herein. In one example, the PCS 104 may be used to note a dosage of medicine given to the patient 116 at a particular time. The PCS 104 and/or patient monitoring device 106 may have a clock, which may be synchronized with an external time source such as a network or a satellite to prevent the EMS technician from having to manually enter a time of treatment or observation (or having to attempt to estimate the time of treatment for charting purposes long after the treatment was administered), according to embodiments of the present disclosure. The PCS 104 may also be used to record biographic and/or demographic and/or historical information about a patient, for example the patient's name, identification number, height, weight, and/or medical history, according to embodiments of the present disclosure. According to embodiments of the present disclosure, the PCS 104 is a tablet PC, such as for example the TabletPCR component of the RescueNet® ePCR Suite available from ZOLL® Data Systems of Broomfield, Colorado According to some embodiments of the present disclosure, the PCS 104 is a wristband or smart phone such as an Apple iPhone or iPad with interactive data entry interface such as a touch screen or voice recognition data entry that may be communicably connected to patient charting system 104 and tapped to indicate what was done with the patient 116 and when it was done. According to some embodiments of the present disclosure, a patient charting device can be integrated with the patient monitoring device 106 and/or the PCS 104, such that a single device can be configured to monitor the patient, treat the patient, as well as to generate records and/or notes about the patient's 116 condition and/or treatments applied to the patient.

The navigation device 110, the PCS 104, and the monitoring device 106 are each useful to the EMS drivers 112 and technicians 114 before, during, and after the patient transport. A patient charting system ("PCS") device 104 may receive, organize, store, share, distribute, and display data from each device 106, 110 to further enhance the usefulness of each device 106, 110 and to make it much easier for the EMS technician 114 to perform certain tasks that would normally require the EMS technician 114 to divert visual and manual attention to each device 106, 110 separately, according to embodiments of the present disclosure. In other words, the PCS device may centralize, organize, and share information that would normally be de-centralized and disorganized, according to embodiments of the present disclosure.

PCS 104 may be a device with embedded or installed software that runs applications that implement the patient charting system capabilities described here, or PCS 104 may be a general purpose tablet or other computing device, or other mobile device, that accesses the patient charting system 104 via a server or cloud interface, according to embodiments of the present disclosure.

The PCS device 104 is communicably coupled to the patient monitoring device 106, and the navigation device 110, according to embodiments of the present disclosure. The PCS device 104 may also be communicably coupled to a storage medium 118. The PCS device 104 may be a touch-screen, flat panel PC or mobile computing device, and the storage medium 118 may be located within or external to the PCS device 104, according to embodiments of the present disclosure. The PCS device 104 may include a display template serving as a graphical user interface, which permits the user (e.g. EMS tech 114) to select different subsets and/or display modes of the information gathered from and/or sent to devices 106, 110, according to embodiments of the present disclosure.

According to embodiments of the present disclosure, the PCS device 104 may not only seamlessly integrate information from a patient monitoring device 106, and/or a navigation device 110 for display and/or use in mobile environment 101, but it may also do so for display in a remote environment such as, for example, enterprise environment 102. Enterprise environment 102 may be a hospital and/or dispatch environment, for example.

Data from the PCS device 104 (and, when present, data from any devices 106, 110 that may be communicably coupled with the PCS device 104) may be received by one or more enterprise storage servers 126 in an administration environment 103 and stored in an enterprise database 130, and the same information may be accessed and provided by one or more enterprise application servers 128 to a workstation 122 of an enterprise user 124, according to embodiments of the present disclosure. According to embodiments of the present disclosure, the PCS device 104 may be communicably coupled to the storage server 126 which may be communicably coupled to the database 130, and the application server 128 is communicably coupled to the database and to the enterprise workstation 122. Such devices may be communicably coupled via a network 120 such as, for example, the Internet.

When the PCS device 104 receives updated information from one or more of the devices (e.g. devices 106, 110) to which it is communicably coupled, and/or via user 114 input, the PCS device 104 sends the updated information to the enterprise storage server 126, which stores the updated information in a database which may be contained on a storage medium 130, according to embodiments of the present disclosure. Hence, information from one or more devices (e.g. devices 106, 110) may be stored in mobile database 118, remote enterprise database 130, or both, according to embodiments of the present disclosure. An enterprise user 124, who may be an emergency room nurse monitoring and/or preparing for ambulance arrivals, an emergency room physician, and/or a medical director at home, for example, may access information similar to information displayed by the PCS device 104 by requesting the information via an enterprise workstation 122. For example, the enterprise workstation 122 accesses a web interface and/or thin client web browser application which requests the information over the network 120 from application server 128. Application server 128 queries the database 130 for the information, and returns a display to enterprise workstation 122 that looks the same as or similar to what the EMS technician 114 is currently seeing on the PCS device 104 display, according to embodiments of the present disclosure.

PCS device 104 can also share information with one or more of the devices (e.g., devices 106, 110). For example, information generated from one of the devices 106, and/or 110 can be collected and then shared with one or more of the other devices. PCS device 104 can also receive information from enterprise application server 128, and/or enterprise storage server 126, and either display such information itself, or share such information with devices 106, and/or 110. For example, if patient monitoring device 106 takes an ECG reading of a patient, or if the patient monitoring device 106 administers a treatment (such as medication or a defibrillation shock), the ECG reading and/or treatment can be shared, via PCS device 104 or directly, with other devices and/or for storage in a patient record maintained therein. In another example, PCS device 104 can be configured to receive patient information, such as medical records, known medical conditions, and biographical information, and to share this information with devices 106, and/or 110. This biographical information can be inserted into a patient record being maintained in the PCS 104.

Although FIG. 1 depicts a single PCS device 104 in the mobile environment 101, in certain embodiments more than one PCS device 104 may be used in the mobile environment 101 to communicably connect to the same or a different set of devices 106, 110. And although FIG. 1 depicts one mobile environment 101, more than one mobile environment 101 and/or more than one PCS device 104 may be communicably coupled with the administration environment 103 and/or the enterprise storage server 126, according to embodiments of the present disclosure. According to embodiments of the present disclosure, the enterprise storage server 126 may receive EMS device information from PCS device 104 and store it in database 130 along with an authenticated time stamp and an identifier associating the information with a particular EMS device and/or a particular EMS vehicle. In this way, data from multiple vehicles and/or multiple devices may be accessed by the enterprise user 124.

Also, the enterprise storage server 130 may securely store the information received from one or more PCS devices 104 for longer periods of time to permit later use of the information. For example, the PCS device 104 may receive patient-identifying information such as name, address, and/or social security number via user input directly into the PCS device 104, and then may convey some or all of the patient-identifying information to enterprise storage server 126 with a request for the enterprise storage server 126 to query the database 130 for past records involving the same patient 116. In other embodiments, PCS 104 receives information in other ways, including without limitation wired or wireless communication and/or messaging.

The enterprise storage server 126 may then forward any such records or portions of such records back to the PCS device 104 (e.g. for display in the patient charting screen or the Past Medical History in the patch notes screen) to assist the EMS technician 114 with the current emergency. Similarly, such past EMS encounter record information may also be accessed by the enterprise user 124, according to embodiments of the present disclosure. A system administrator 134 may access and/or monitor the data in database 130 and/or modify the instructions of the servers 126, 128 via administration workstation 132, which may be communicably coupled to the servers 126, 128, according to embodiments of the present disclosure.

According to some embodiments of the present disclosure, the PCS device 104 may connect with (e.g. automatically or manually or selectively) a wearable medical device, such as, for example, a Lifevest® wearable defibrillator, to receive and display patient monitoring information therefrom. The PCS device 104 may also be configured to receive patient-identifying information from such a wearable device, to permit the PCS device 104 to query an external database, for example across network 120, to retrieve additional information about the patient. The PCS device 104 may also be configured to connect with an implantable cardioverter-defibrillator ("ICD") in a similar fashion, according to embodiments of the present disclosure.

Further details regarding systems similar to system 100 can be found in US Patent Application Publication No. 2011/0172550, titled "SYSTEMS AND METHODS FOR EMS DEVICE COMMUNICATION INTERFACE," published Jul. 14, 2011, the entire contents of which are incorporated herein by reference.

Some embodiments of the present disclosure include various steps, some of which may be performed by hardware components or may be embodied in machine-executable instructions. These machine-executable instructions may be used to cause a general-purpose or a special-purpose processor programmed with the instructions to perform the steps. Alternatively, the steps may be performed by a combination of hardware, software, and/or firmware, on one device and/or distributed across multiple devices and/or processors. In addition, some embodiments of the present disclosure may be performed or implemented, at least in part (e.g., one or more modules), on one or more computer systems, mainframes (e.g., IBM mainframes such as the IBM zSeries, Unisys ClearPath Mainframes, HP Integrity NonStop servers, NEC Express series, and others), or client-server type systems. In addition, specific hardware aspects of embodiments of the present disclosure may incorporate one or more of these systems, or portions thereof.

Figure 2:
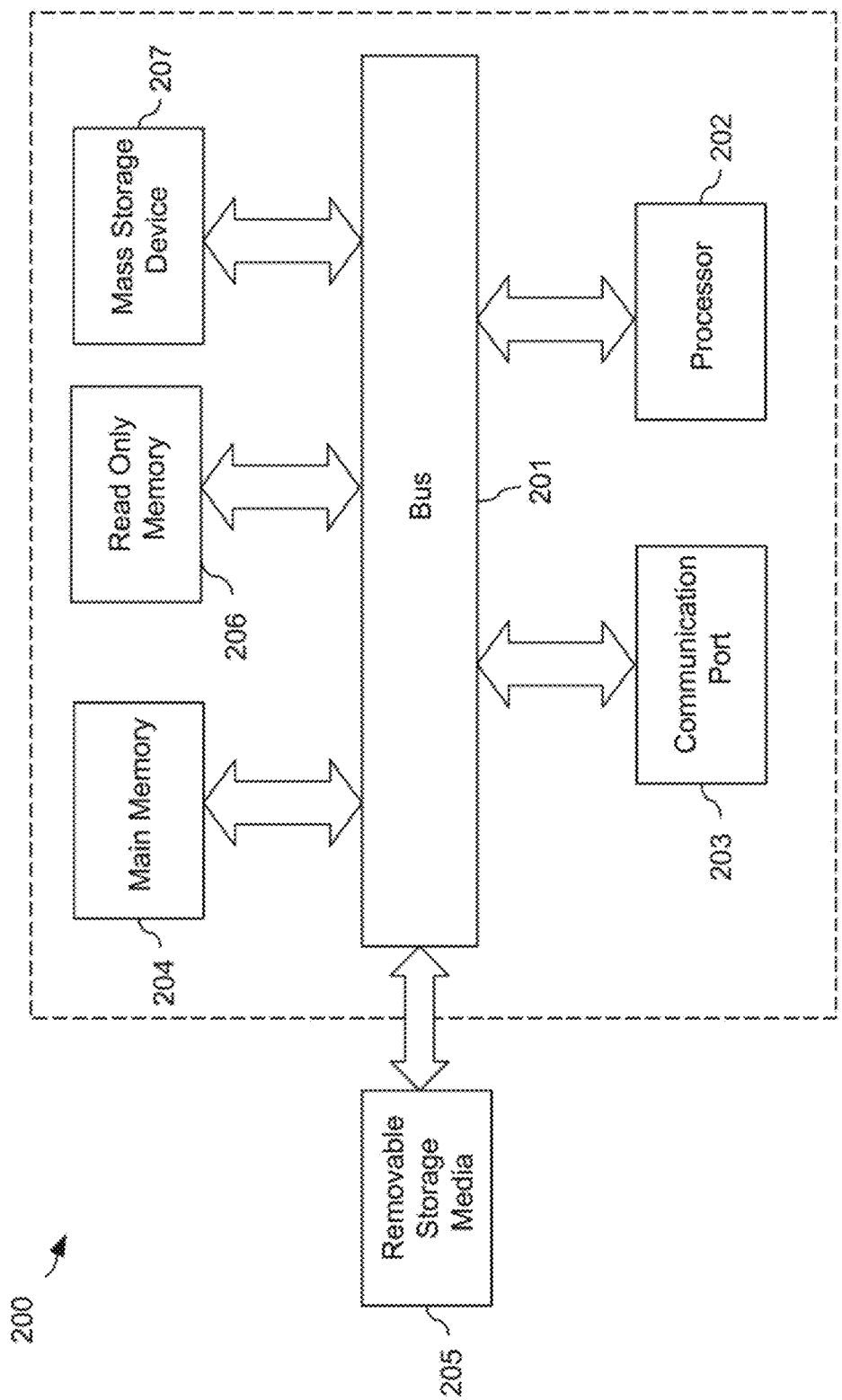
FIG. 2 is an example of a computer system with which embodiments of the present disclosure may be utilized.

As such, FIG. 2 is an example of a computer system 200 with which embodiments of the present disclosure may be utilized. System 200 may be a desktop, notebook, mobile, portable, or other type of computing system. According to the present example, the computer system includes a bus 201, at least one processor 202, at least one communication port 203, a main memory 204, a removable storage media 205, a read only memory 206, and a mass storage 207.

Processor(s) 202 can be any known processor, such as, but not limited to, an Intel® Itanium® or Itanium 2® processor(s), or AMD® Opteron® or Athlon MP® processor(s), or Motorola® lines of processors. Communication port(s) 203 can be any of an RS-232 port for use with a modem based dialup connection, a 10/100 Ethernet port, or a Gigabit port using copper or fiber, for example. Communication port(s) 203 may be chosen depending on a network such a Local Area Network (LAN), Wide Area Network (WAN), or any network to which the computer system 200 connects. Main memory 204 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, hard disks such as the Adaptec® family of SCSI drives, an optical disc, an array of disks such as RAID (e.g. the Adaptec family of RAID drives), or any other mass storage devices may be used, for example. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, IOMEGA® Zip Drives, Compact Disc-Read Only Memory (CD-ROM), Compact Disc-Re-Writable (CD-RW), or Digital Video Disk-Read Only Memory (DVD-ROM), for example. The components described above are meant to exemplify some types of possibilities. In no way should the aforementioned examples limit the scope of the disclosure, as they are only exemplary embodiments.

Figure 3:
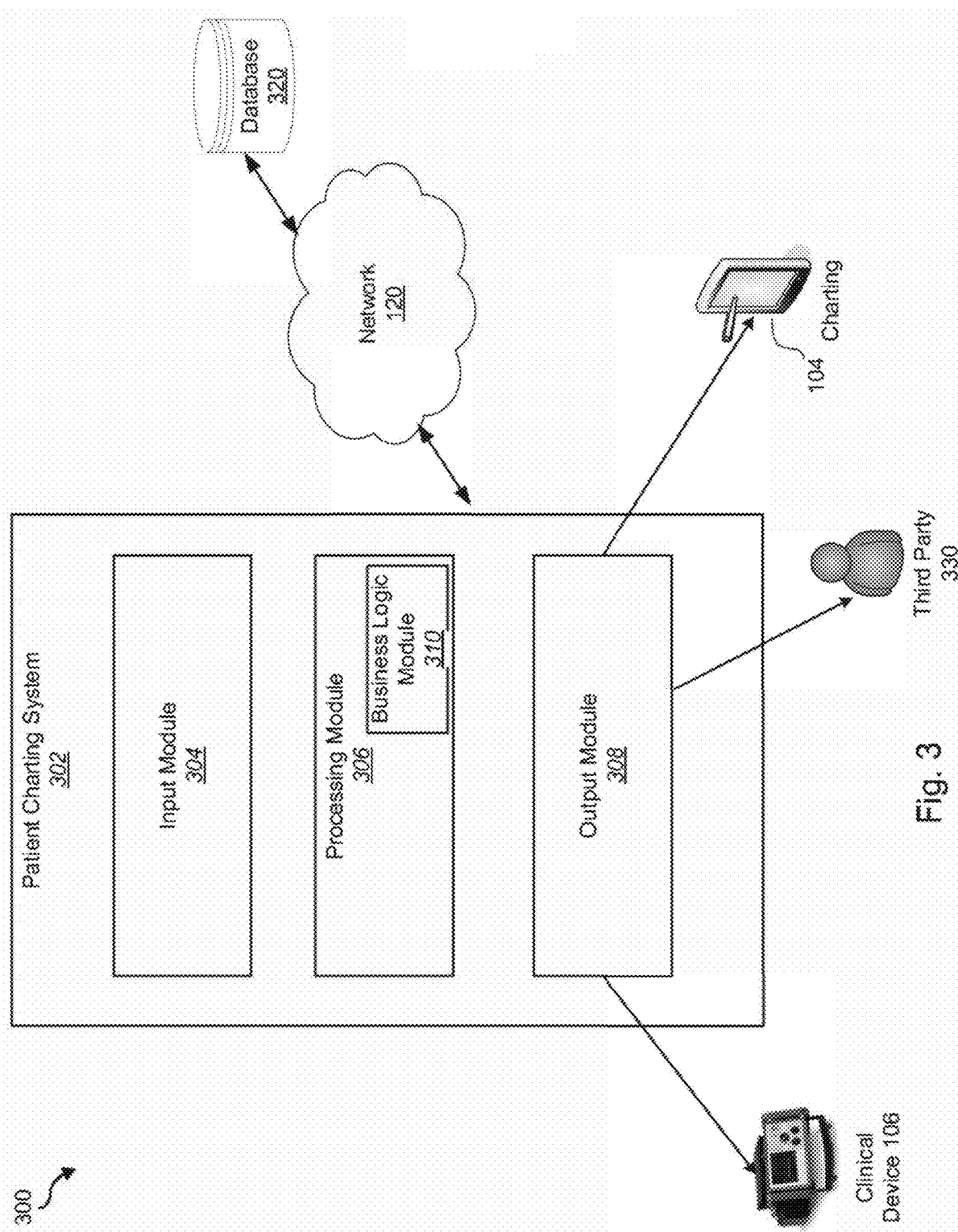
FIG. 3 illustrates a block diagram illustrating a patient charting system in accordance with an embodiment of the present disclosure.

FIG. 3 illustrates a block diagram illustrating a patient charting system in accordance with an embodiment of the present disclosure. Patient charting system 302 may be one or a combination of hardware, software, an application, and a device (e.g. system 200), according to some embodiments of the present disclosure. Features, functionality, and capabilities described herein with respect to PCS 104 also apply to patient charting system 302 and other systems described herein, and features, functionality, and capabilities described herein with respect to patient charting system 302 also apply to PCS 104 and other systems described herein, according to embodiments of the present disclosure. Patient charting system 302 may reside on a client, such as an end-user device, and/or a server, such as a web server. One or more portions of patient charting system 302 may reside on different computers. One or more portions of the patient charting system 302 may reside at a network centric location. According to some embodiments, analysis and approval of resource references including patient charting system 302 may be implemented as part of a cloud computing environment. For example, patient charting system 302 may be distributed to various clients and servers through a cloud computer environment. As another example, patient charting system 302 may be updated at the network centric location and then distributed to various clients and servers. According to some embodiments and FIG. 2, patient charting system 302 may include system 200 and/or may be resident in main memory 204. Patient charting system may comprise one or more processors. As used herein, "module" is used in its broadest sense to refer to hardware, software, firmware, and/or a combination of two or more of hardware, software, and firmware. In some cases, a module that is part of a system is a device that performs the described functionality. In other cases, a module that is part of a system is a set of instructions, and/or a memory with those instructions, that, when executed by a processor, performs the described functionality.

In some embodiments, patient charting system 302 may include input module 304, processing module 306, and output module 308. Processing module 306 may include business logic module 310. Input module 304, processing module 306, and output module 308 may reside on different computers and/or devices. For example, input module may reside on a client device of an emergency medical service personnel. Processing module 306 may reside at a server. Portions of a module may reside on different computers as well. For example, some portion of output module 308 may reside on a server, and some portion of output module 308 may reside on a client device.

Input module 304 may receive charting data. Charting data may include, but is not limited to, patient information (e.g., name, age), medical event specific information (e.g., type of service requested, disposition) and clinical information (e.g., patient assessment, patient blood pressure). Charting data may be received via various mechanisms, including, but not limited to, touch-screen, voice recognition, and scanner. For example, a patient may say his/her name and input module 304 may capture the patient name and save it in the patient charting system. Input module 304 may be coupled to a scanner through which patient's driver license may be scanned and relevant information about the patient, such as name, address, age, may be saved in the patient charting system. A caregiver may dictate data or findings when examining the patient. Such dictation may be captured by input module 304 and saved in the patient charting system 302, according to some embodiments. As used herein, the phrases "medical situation" and "medical event" are used in their broadest sense to refer to and may include any situation or event in which medical attention is called for, in which a patient experiences a medical problem, or in which a patient has treatment or care, and includes, for example, emergent situations. For example, and without limitation, a medical event may begin when a patient experiences medical symptoms and a call is made to emergency services (e.g. emergency medical services), and the medical event may end when the patient has been evaluated, treated, transported, and/or released. A medical event or situation may include various events within the medical event, including for example emergency transport. As used herein, "clinical data" is used in its broadest sense to refer to data relevant in treatment and/or diagnosis of a patient, and may include both physiological data and vital signs, for example. Non-clinical data, or data of a non-clinical type, is data that is not clinical data; for example, data of a non-clinical type includes biographical data such as name, address, patient identification number, and/or the like.

Processing module 306 may obtain additional data that is associated with at least some of the received charting data. Processing module 306 may make smart decisions as to where to retrieve additional data from. For example, such decisions may be based on the received patient address, processing module 306 may retrieve patient medications from a pharmacy that is close to the patient address. Processing module 306 may retrieve additional data using health data exchange standards, such as state-wide health data exchange standards, regional health data exchange standard, HL7 message standards, and NCPDP script standards. Processing module 306 may retrieve additional data using communication protocols over network (e.g., via network 120, from remote database 320), including, but not limited to, SOAP, RESTFul, and Web Services. Processing module 306 may retrieve additional data within the same organization or network of which it is a part, or from at least one other organization or network or third party source. Processing module 306 may retrieve additional data from various providers, including, but not limited to, hospitals, clinics, doctors' offices, and pharmacies.

In some embodiments, processing module 306 may include business logic module 310. Business logic module 310 may be coupled to a data source that stores rules that customizes a template of patient charting system 302. The data source may be a file, a database, and/or the like. Business logic module 310 may also be a software module that implements business logic to customize a template of patient charting system 302. For example, if received charting data (e.g., input by a user of patient charting system 302) indicates that patient's gender is male, then processing module 306 may customize a template such that a data field relating to current pregnancy is greyed out or otherwise deactivated, and/or defaulted as "No."

Output module 308 may send charting data and/or additional data to PCS 104, third party 330, and/or clinical device 106. In some embodiments, charting data and/or additional data may be sent over a network. Patient charting system 302 may be a web application. A portion of output module 308 may be a web page that can be displayed on, for example, PCS 104, or a client device for third party 330. Patient charting system 302 may be implemented based on a server and client architecture. A portion of patient charting system 302, for example output module 308 or a portion of output module 308 may be implemented as, for example, an Android application or an Apple Application operable on a smart phone. Output module 308 may communicate with clinical device 106 via specific protocols.

Figure 4:
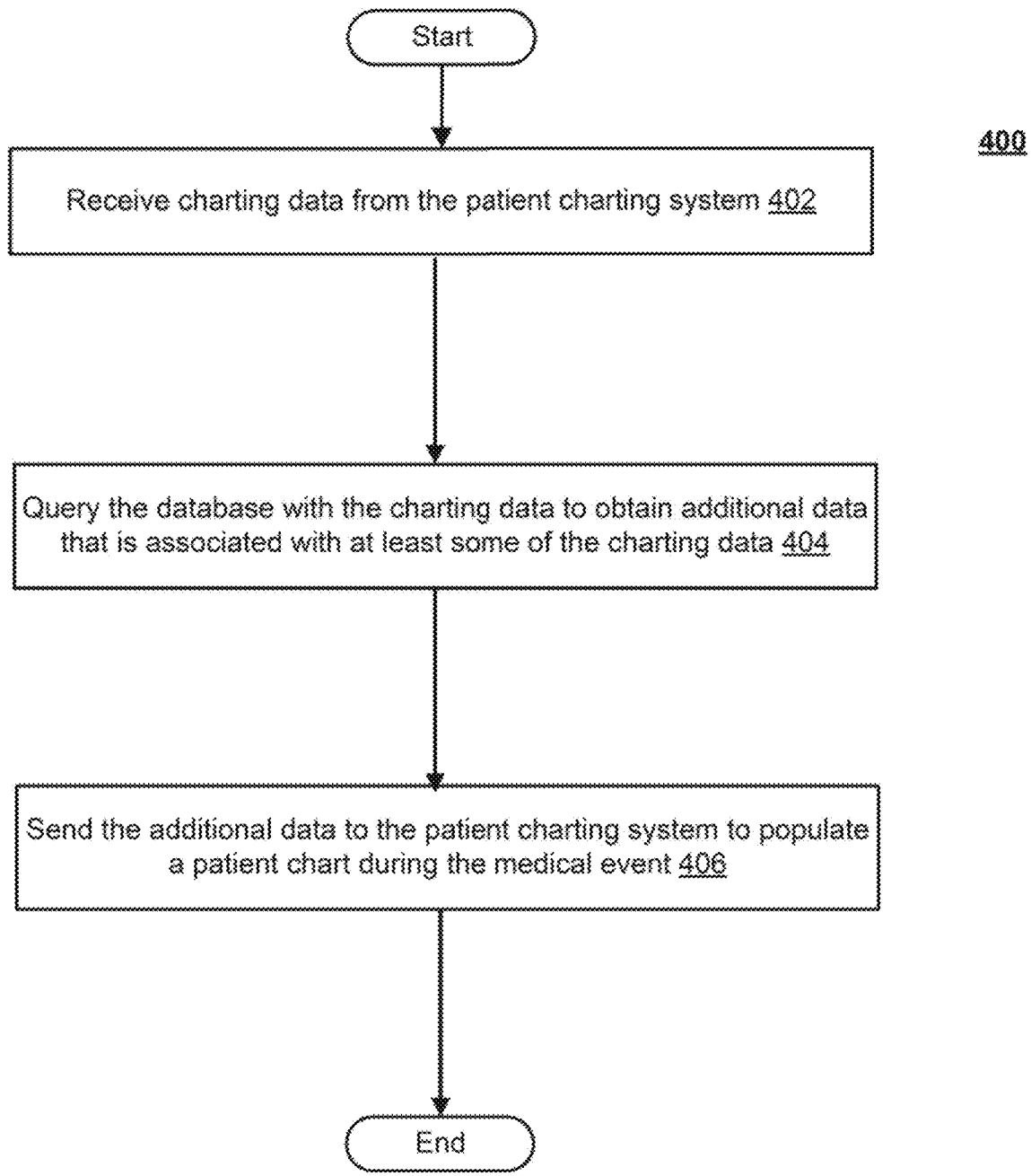
FIG. 4 illustrates an exemplary process of the patient charting system of obtaining additional data to populate a patient chart, according to some embodiments.

FIG. 4 illustrates an exemplary process of the patient charting system of obtaining additional data to populate a patient chart, according to some embodiments. As described in additional detail below, process 400 may include receiving charting data from the patient charting system (block 402), querying the database with the charting data to obtain additional data that is associated with at least some of the charting data (block 404), and sending the additional data to the patient charting system to populate a patient chart during the medical event (block 406).

Process 400 may receive charting data from the patient charting system (block 402). Charting data may include, but is not limited to, information about the patient (e.g., name, address), information about the medical event (911 response, ground transportation), clinical information (patient assessment, patient vital signs), and caregiver information (e.g., name of emergency medical service personnel). Data may include data of a clinical type, and/or data of a non-clinical type. As used herein, the term "clinical" is used in its broadest sense to refer to that which is directly implicated in monitoring or treatment or diagnosis of a patient. As used herein, the term "non-clinical" is used in its broadest sense to refer to that which is not directly implicated in monitoring or treatment or diagnosis of a patient. For example, a defibrillator is a clinical device, and a navigation device is a non-clinical device. As another example, a patient's ECG information or heart rate is clinical information, while a patient's address is non-clinical information.

Process 400 may query the database with the charting data to obtain additional data that is associated with at least some of the charting data (block 404). In some embodiments, since a query with patient name may not identify the correct patient, process 400 may query, in addition to patient name, address, gender, birthdate and/or age. Process 400 may query with a patient identifier. Additional data obtained may include patient medications and/or patient medication allergies. Additional data obtained may also include information besides the patient or the patient's identity. For example, a user may enter name of a destination health facility as charting data, and process 400 may obtain the address of the destination healthcare facility.

Process 400 may send the additional data to the patient charting system to populate a patient chart during the medical event (block 406). For example, process may query with patient name, gender, and/or age, and obtain additional data including patient address, medications, medication allergies, previous treatment history, and/or primary physician information. Such additional data may be sent to populate a patient chart. In some embodiments, additional data population is visible. For example, data field "patient address" may be visibly populated. In other embodiments, additional data population may not be visible. In other words, additional data is obtained and sent to the patient charting system, but not visually displayed on the patient chart. However, additional data may be populated in the sense of being stored as part of a patient record associated with the patient chart. For example, medication allergies may not be visually displayed, or visually displayed at all times, on the patient chart, but stored as part of the patient record associated with the patient chart.

Process 400 may be modified by removing, adding, or rearranging any of the aforementioned stages. For example, process 400 may be modified by removing the step of querying the database. In other words, additional data may be obtained without querying the database. For example, if charting data indicates the patient is male, then process 400 may obtain additional data of the patient not pregnant without querying the database, through software implementation. Process 400, as well as the other processes described herein, may also be performed in an order other than the order shown or described, and may eliminate steps and/or add steps.

Figure 5:
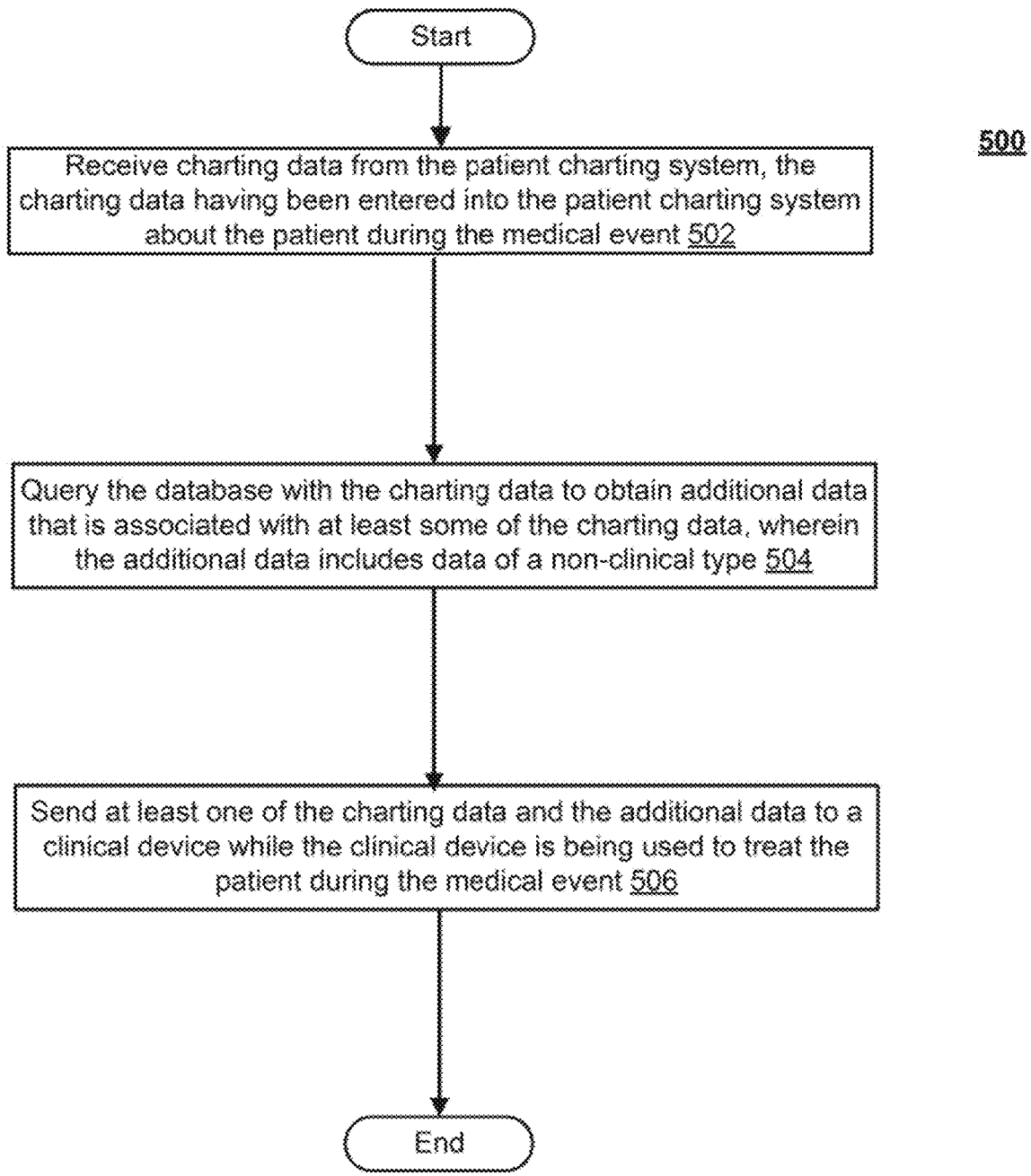
FIG. 5 illustrates an exemplary process of the patient charting system of sending additional data to a clinical device, in accordance with an example method of the present disclosure, according to some embodiments.

FIG. 5 illustrates an exemplary process of the patient charting system of sending charting data and/or additional data to a clinical device, in accordance with an example method of the present disclosure, according to some embodiments. Process 500 may include: receive charting data from the patient charting system, the charting data having been entered into the patient charting system about the patient during the medical event (block 502); query the database with the charting data to obtain additional data that is associated with at least some of the charting data, wherein the additional data includes data of a non-clinical type (block 504); and send at least one of the charting data and the additional data to a clinical device while the clinical device is being used to treat the patient during the medical event.

Process 500 may receive charting data from the patient charting system, the charting data having been entered into the patient charting system about the patient during the medical event (block 502). As described above, the charting data may include, but is not limited to, patient information, medical event information, clinical information, and caregiver information.

Process 500 may query the database with the charting data to obtain additional data that is associated with at least some of the charting data, wherein the additional data includes data of a non-clinical type (504). For example, process 500 may query with a patient identifier and obtain an address of the patient. In some embodiments, the additional data includes an identifier of the device. In one embodiment, the charting data includes a location of the patient and the additional data includes identification information of the clinical device that is at the location. In this embodiment, if the clinical device is at the same location as the patient, the clinical device may be used to treat the patient. With the identifier and/or identification information of the device, process 500 may communicate with the device (e.g., send data to the device). This may be analogous to communicating with a device identified with an IP address, according to some embodiments.

Process 500 may send at least one of the charting data and the additional data to a clinical device while the clinical device is being used to treat the patient during the medical event (block 506). In some embodiments, the clinical device is a defibrillator or a monitor defibrillator. For example, the defibrillator may be the one that is equipped with the ambulance the patient is in. An example defibrillator may be a ZOLL® X Series® Defibrillator. The defibrillator may be a wearable defibrillator, such as ZOLL® LifeVest®. The defibrillator, and/or a patient monitor, may be configured to gather data about a patient, for example electrocardiogram or 12-lead data. Physiological data includes data collected from a patient relating to the function of that patient's body systems, including without limitation the type of data acquired by a patient monitor and/or defibrillator. Non-physiological data is data that is not physiological data. In some embodiments, the clinical device is a resuscitation monitoring and assistance device, such as ZOLL® AutoPulse Resuscitation System. In some embodiments, data such as patient age, gender, and weight is sent to the clinical device. Such data may be required by the clinical device. In other embodiments, data sent to the clinical device (including, without limitation, data obtained from a charting device or from a server with which the charting device communicates) may comprise clinical charting or treatment history data of the patient, such as medical conditions, medical history, and/or medications. This data may modify the clinical operation of the device. For example, if the patient is on a medication that lowers a heart rate, then a defibrillator (e.g., ZOLL® LifeVest), while monitoring the patient's heart rhythm, may in some cases take the medication factor into consideration. If the patient had a heart attack not too long ago, then a defibrillator (e.g., ZOLL® LifeVest), while monitoring the patient's heart rhythm, may need to elevate the risk assessment of cardiac arrest. A defibrillator may adjust strength of electrical currency when applying electrical shocks depending on the patient weight. Likewise, a resuscitation monitoring and assistance system (e.g., ZOLL® AutoPulse Resuscitation System) may adjust squeeze or compression force over a patient chest depending on the patient age. In some embodiments, patient information may be used to influence the decisions that the medic makes while evaluating and/or treating the patient.

Figure 6:
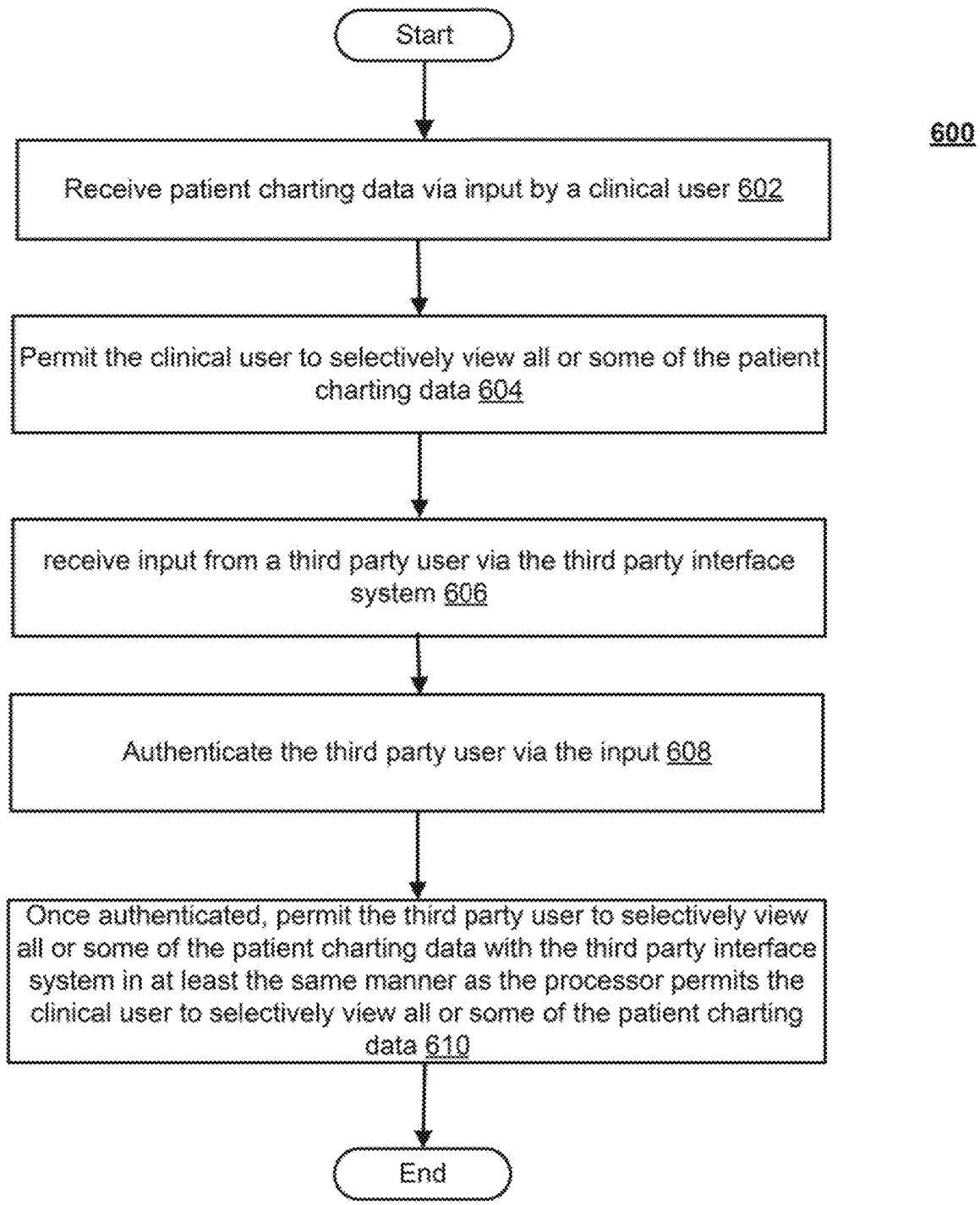
FIG. 6 illustrates an exemplary process of the patient charting system of enabling a third party to view the patient chart, according to some embodiments.

FIG. 6 illustrates an exemplary process of the patient charting system of enabling a third party to view the patient chart, according to some embodiments. Process 600 may include receiving patient charting data via input by a clinical user (block 602), permitting the clinical user to selectively view all or some of the patient charting data (block 604), receiving input from a third party user via the third party interface system, which may be, for example, system 200 (block 606), authenticating the third party user via the input (block 608), and once authenticated, permit the third party user to selectively view all or some of the patient charting data with the third party interface system in at least the same manner as the processor permits the clinical user to selectively view all or some of the patient charting data (block 610).

Process 600 may receive patient charting data via input by a clinical user (block 602). In some embodiments, the clinical user of the patient charting system may be the emergency medical service personnel who is treating the patient on the scene or in the ambulance. The clinical user may enter information regarding the patient and event.

Process 600 may permit the clinical user to selectively view all or some of the patient charting data (block 604). In some embodiments, the clinical user may select the view to adapt to the charting device that he is using. For example, if the clinical user is using a laptop, the user may select to view all of the patient data. If the user is using a tablet with a smaller screen, the user may select to view a subset of the patient charting.

Process 600 may receive input from a third party user via the third party interface system (block 606). In some embodiments, third parties may be the patient himself, a family member of the patient, an emergency medical service personnel, and/or a healthcare provider. For example, the patient family may request to see the patient charting data so as to understand what has happened to the patient and a current condition of patient (e.g., type and/or severity of the patient injury). An ER doctor of the destination facility may request to see the patient charting data so as to prepare before patient arrival.

Process 600 may authenticate the third party user via the input (block 608). In some embodiments, the input may comprise credentials of the third party, such as name of a family member, name/national physician identifier and office address of a physician. Such credentials may be compared against the patient record. For example, whether the patient has signed a medical release form to allow the family member and/or the physician to access his record. In some embodiments, third party access may be examined to ensure regulatory, such as HIPAA, compliance. In some embodiments, the input may comprise usernames/passwords, security keys, security token, and/or the like. Authentication of the third party may occur in a number of ways. For example, the authentication may require a username and/or password or other login credential, and the system 302 may be configured to encrypt the communication of any medical record data, with a decryption key corresponding to the user's authentication, to permit an authorized third party user to access the data. In other embodiments, the controller of the system 302 may distribute a token or other access credential, either electronically and/or physically, to permit the third party to authenticate. For example, if the patient's next-of-kin present in an emergency wishes to access the patient's charting record for the emergency encounter, the EMS technician who is charting the patient can scan a unique code, such as a bar code or other temporary identifier, from a single-use printed paper card, into the patient chart and hand over the paper card to the next-of-kin to permit the next-of-kin to log in using the same credential. Such authenticated access may also be achieved via one or a combination of other known encryption and/or authentication methods, for example a virtual private network, a Secure Socket Layer connection, or other secured communications channels or protocols.

Process 600 may, once authenticated, permit the third party user to selectively view all or some of the patient charting data with the third party interface system in at least the same manner as the processor permits the clinical user to selectively view all or some of the patient charting data (block 610). In other words, third party users may view the patient charting data similar to the clinical user. In some embodiments, thirty party users may see the patient charting data in real-time or in near real-time as the clinical user inputs the patient charting data. In some embodiments, the third party may be alerted as to the destination healthcare facility to which the patient is transported.

Figure 7:
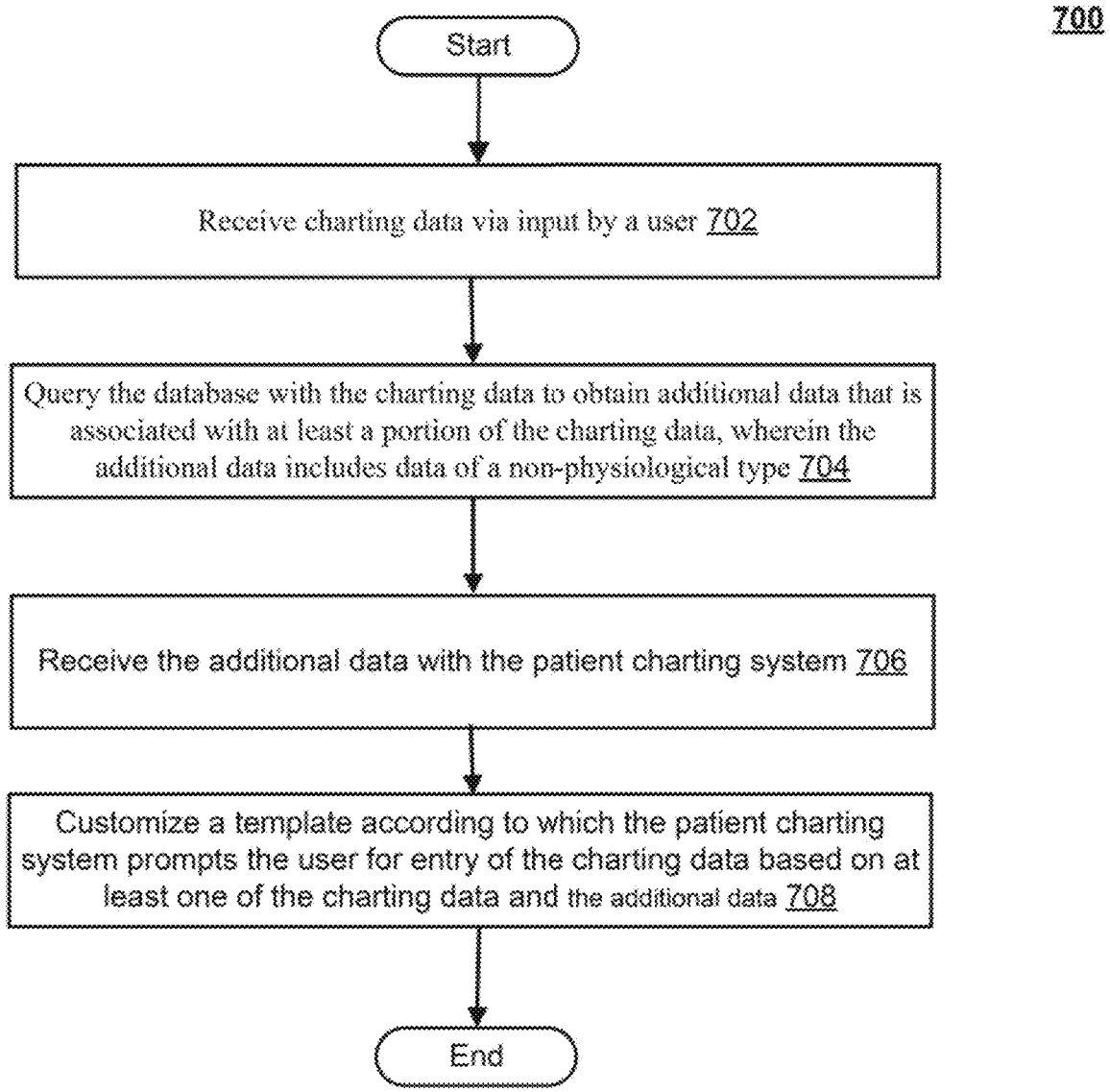
FIG. 7 illustrates an exemplary process of the patient charting system of customizing a template based on user input and additional data, according to some embodiments.

FIG. 7 illustrates an exemplary process of the patient charting system of customizing a template based on user input and additional data, according to some embodiments. Process 700 may include receiving charting data via input by a user (block 702), querying the database with the charting data to obtain additional data that is associated with at least a portion of the charting data, wherein the additional data includes data of a non-physiological type (704), receiving the additional data with the patient charting system (706), and customizing a template according to which the patient charting system prompts the user for entry of the charting data based on at least one of the charting data and the additional data (708).

Process 700 may receive charting data via input by a user (block 702). As described above, charting data may include, but is not limited to, patient information, medical event information, clinical information, and caregiver information.

Process 700 may query the database with the charting data to obtain additional data that is associated with at least a portion of the charting data, wherein the additional data includes data of a non-physiological type (704). In some embodiments, additional data may be obtained without querying the database, for example, pregnancy status.

Process 700 may receive the additional data with the patient charting system (706). The additional data may include, but is not limited to, medication allergies, medications, conditions.

Process 700 may customize a template according to which the patient charting system prompts the user for entry of the charting data based on at least one of the charting data and the additional data (708). In some embodiments, one or more entries may be disabled and/or filled out automatically. In some embodiments, user input may be validated. In some embodiments, the user may be prompted to re-enter data. Block 708 will be described in further detail in relation to FIGS. 8 to 14.

Figure 8:
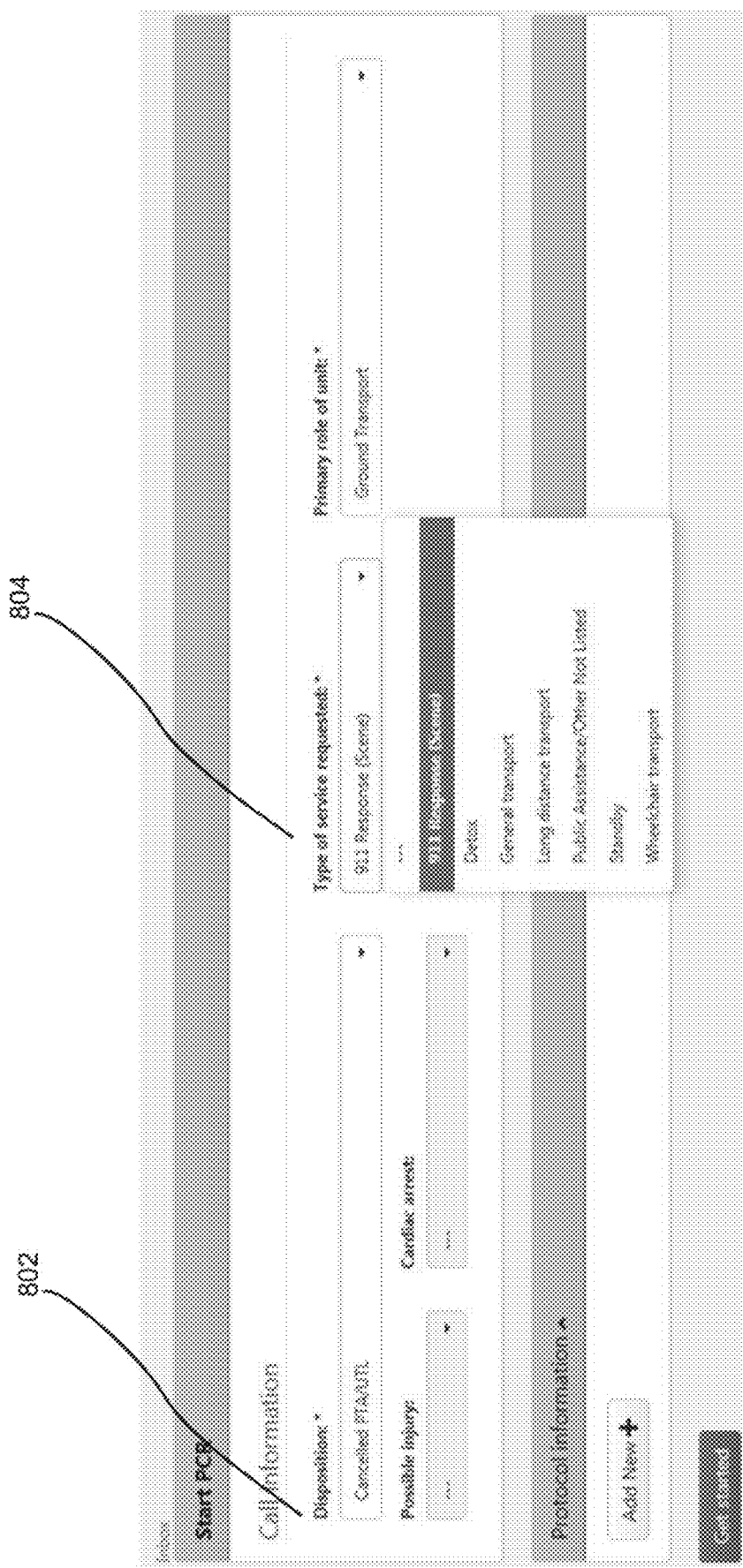
FIG. 8 illustrates an exemplary graphical user interface for the patient charting system, according to some embodiments.

FIG. 8 illustrates an exemplary graphical user interface for the patient charting system, according to some embodiments. As shown in FIG. 8, user input to the "Disposition" field 802 is "Cancelled PTA/UTL," and to the "Type of service requested" field 804 is "911 Response (Scene)." In some embodiments, "Cancelled PTA/UTL" indicates that the medical event is cancelled prior to arrival/until transport live. Accordingly, patient-related entries are disabled (shown in FIG. 9)

Figure 9:
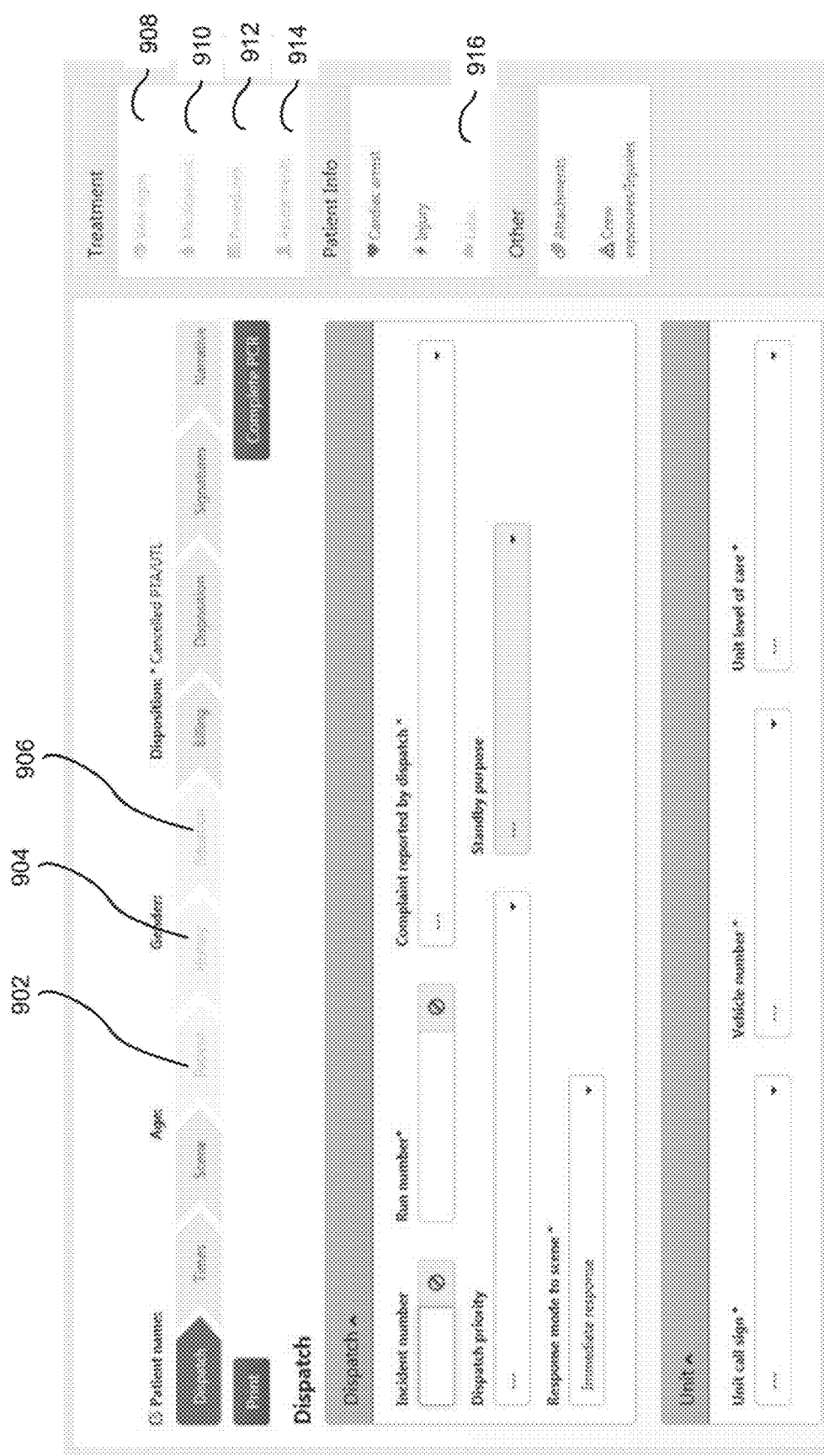
FIG. 9 illustrates an exemplary customized template for the patient charting system in response to user input shown in FIG. 8, according to some embodiments.

FIG. 9 illustrates an exemplary customized template for the patient charting system in response to user input shown in FIG. 8, according to some embodiments. As shown in FIG. 9, in some embodiments, in response to user input that the medical event is cancelled, patient related entries/labs, including "Patient" 902, "History" 904, "Situation" 906, "Vital sign" 908, "Medications" 910, "Procedures" 912, "Assessment" 914, and "Lab" 916 are disabled (e.g., greyed out).

Figure 10:
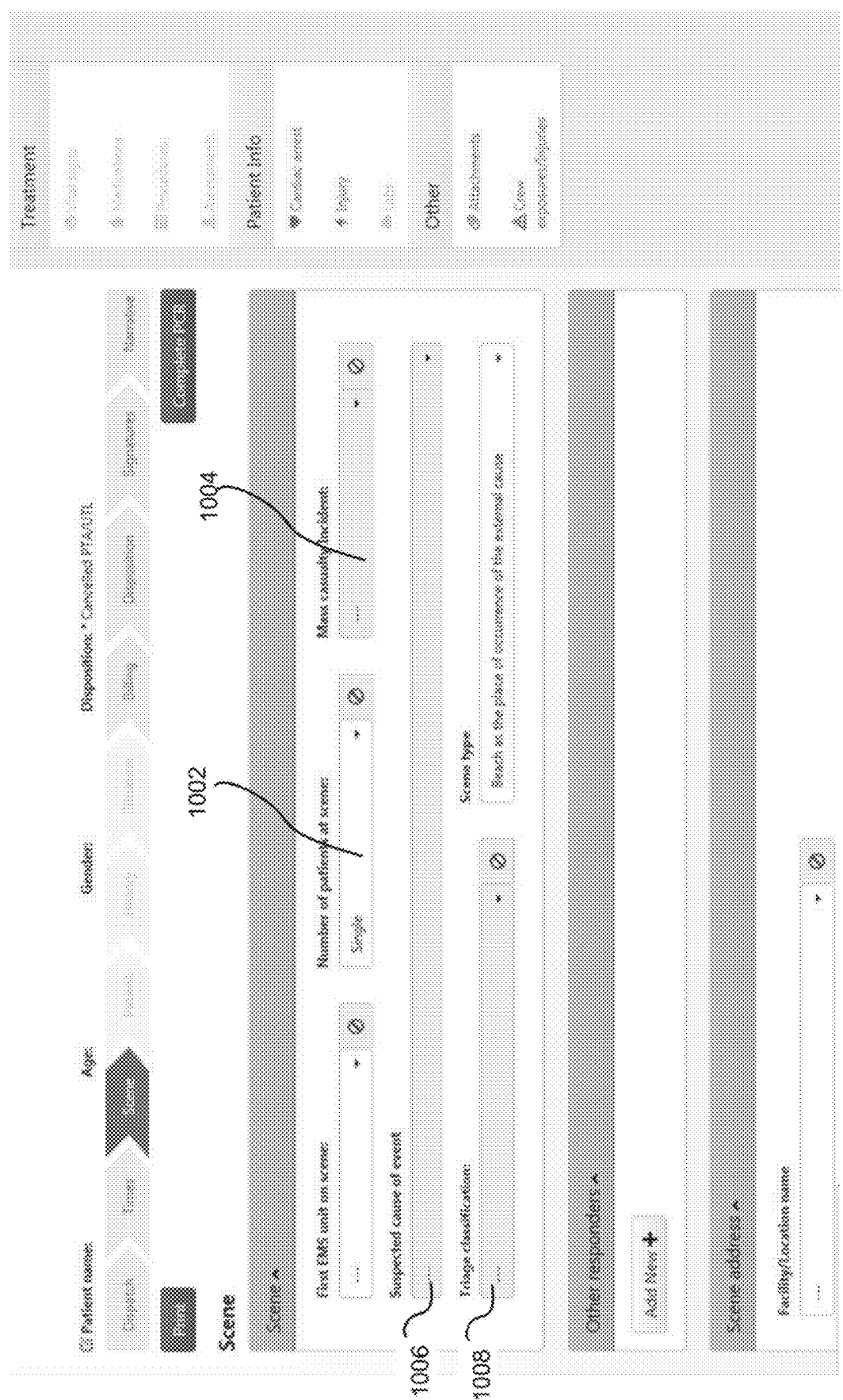
FIG. 10 illustrates an exemplary graphical user interface and customized template for the patient charting system where charting data indicates a single patient, according to some embodiments.

FIG. 10 illustrates an exemplary graphical user interface and customized template for the patient charting system where charting data indicates a single patient, according to some embodiments. As shown in FIG. 10, user input to the "Number of patient at scene" 1002 is "Single." In some embodiments, in response to such user input, entries related to multiple patients, including "Mass casualty incident" 1004, "Suspected cause of event" 1006, and "Triage classification" 1008 are disabled (e.g., greyed out).

Figure 11:
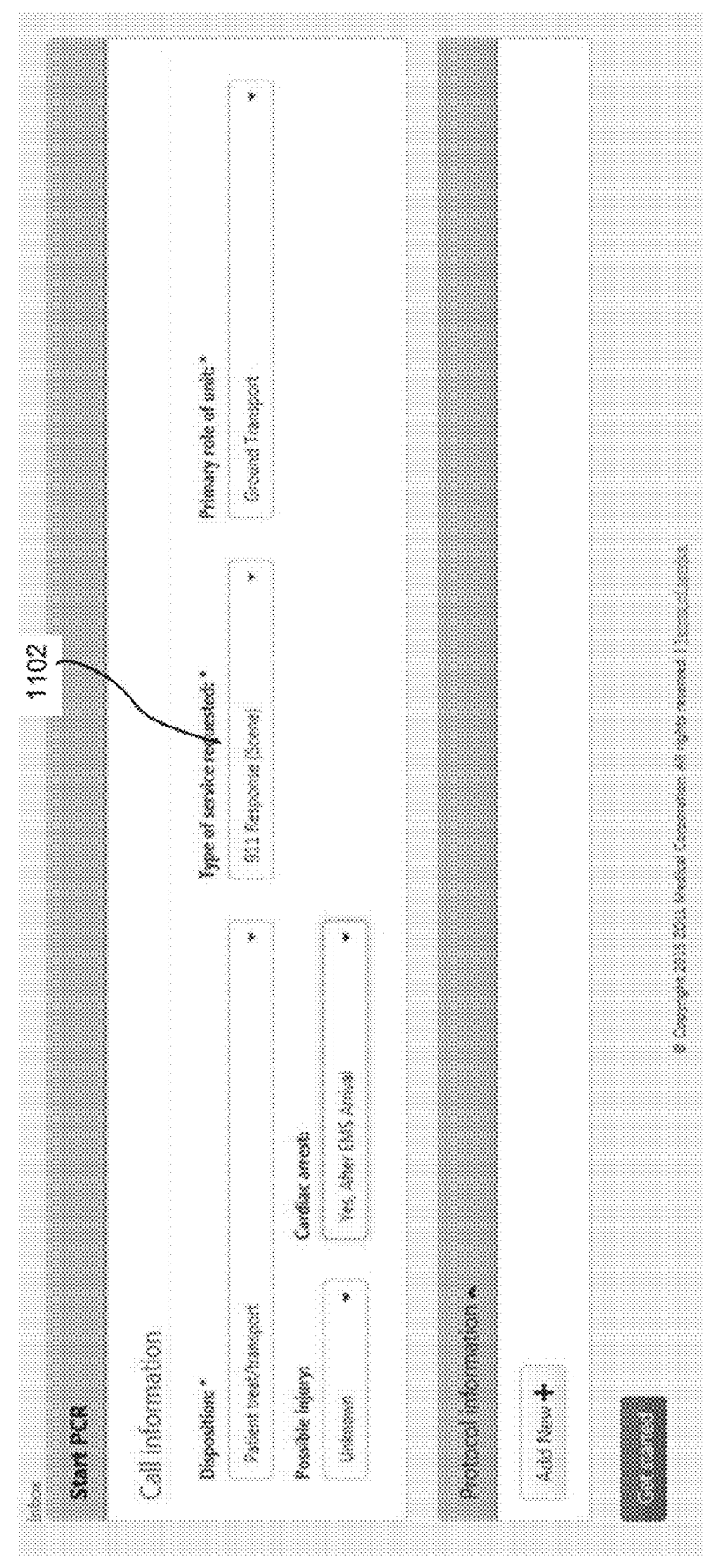

FIG. 11 illustrates an exemplary graphical user interface for the patient charting system where charting data indicates 911 response, according to some embodiments. As shown in FIG. 11, user input to the "Type of service requested" 1102 is "911 Response (Scene)."

Figure 12:
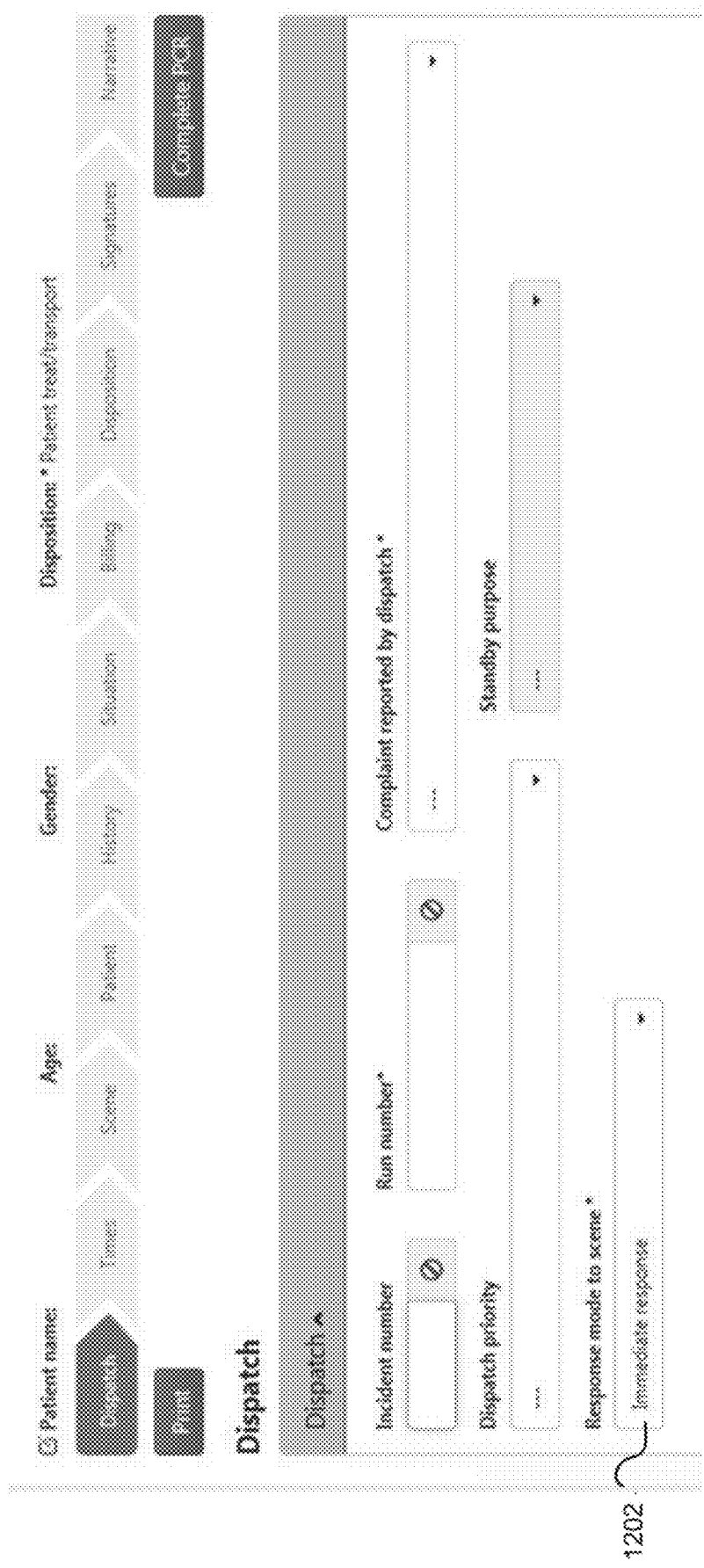
FIG. 12 illustrates an exemplary customized template for the patient charting system in response to user input shown in FIG. 11, according to some embodiments.

FIG. 12 illustrates an exemplary customized template for the patient charting system in response to user input shown in FIG. 11, according to some embodiments. As shown in FIG. 12, in some embodiments, since the "Type of service requested" is "911 Response (Scene)," "Response mode to scene" 1202 is automatically filled out as "Immediate response."

Figure 13:
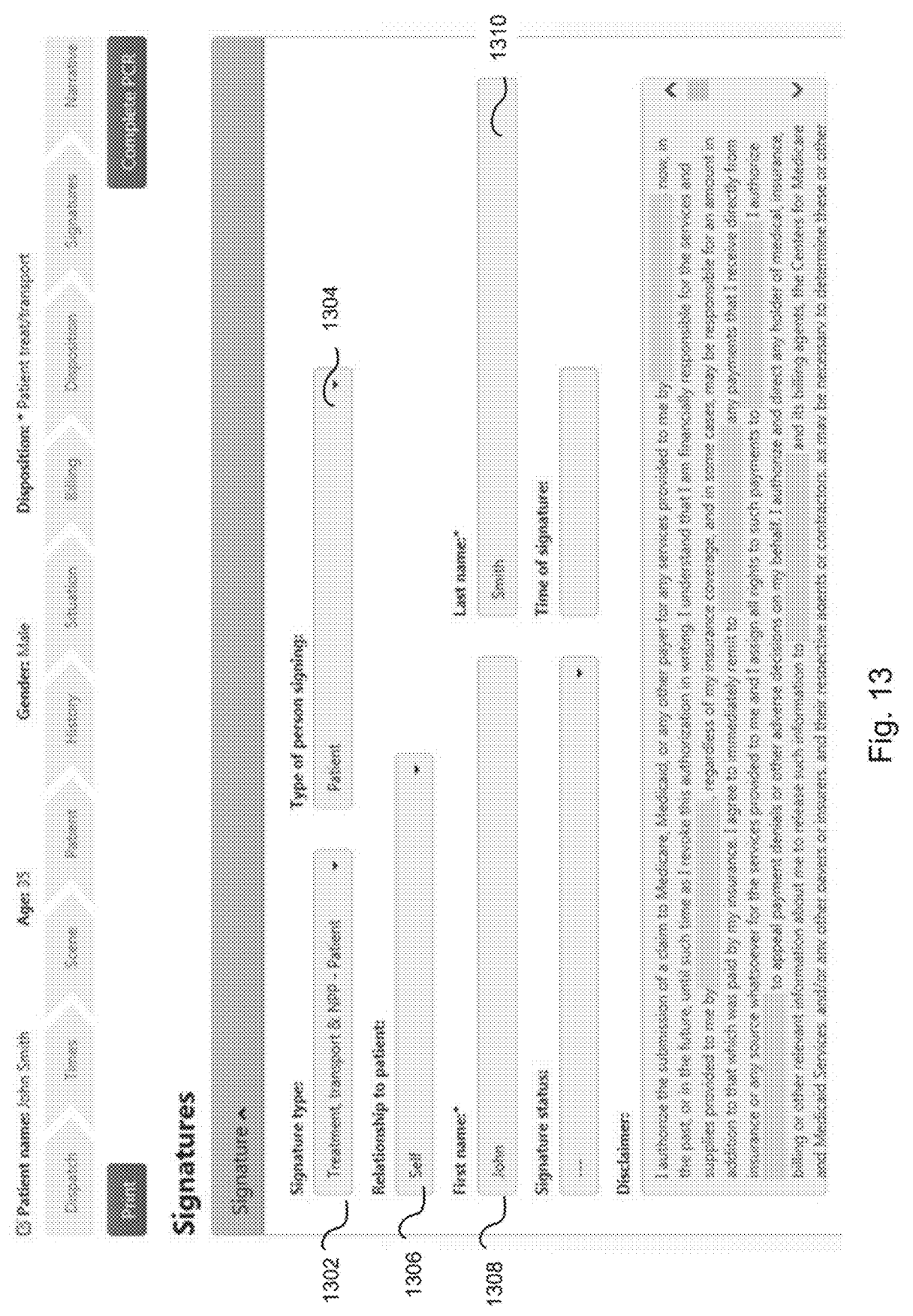

FIG. 13 illustrates an exemplary graphical user interface for the patient charting system where charting data indicates patient signature, according to some embodiments. As shown in FIG. 13, user input to "Signature Type" 1302 is "Treatment, transport & NPP—Patient." In response to such user input, "Type of person signing" 1304 is automatically filled out as "Patient"; "Relationship to patient" 1306 is automatically filled out as "Self"; "First name" 1308 is automatically filled out using patient's first name; and "Last name" 1310 is automatically filled out using patient's last name.

Figure 14:
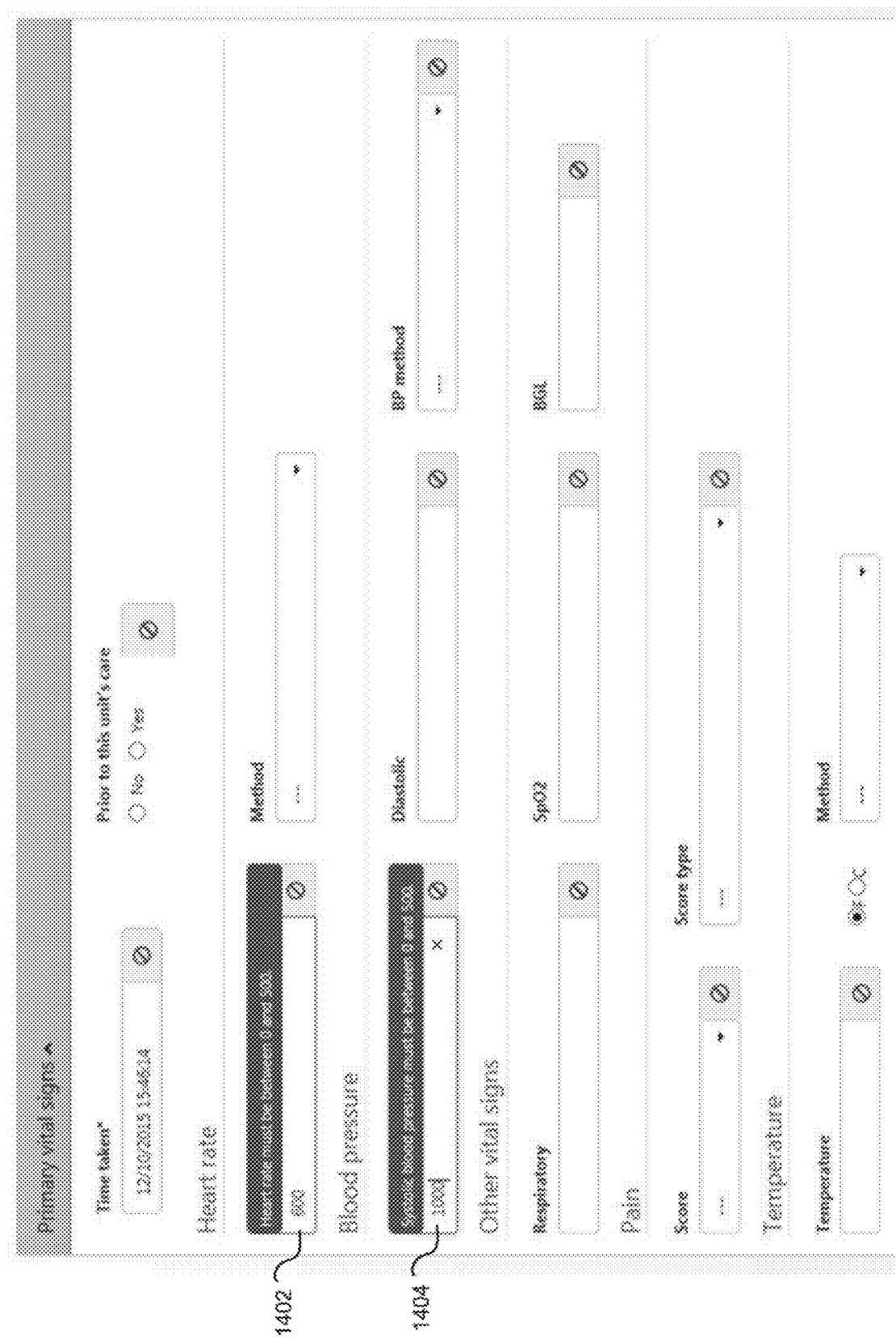
FIG. 14 illustrates an exemplary graphical user interface and customized template for the patient charting system in which user entries are validated, according to some embodiments.

FIG. 14 illustrates an exemplary graphical user interface and customized template for the patient charting system in which user entries are validated, according to some embodiments. User input to "Heart rate" 1402 and "Systolic blood pressure" 1404 is invalid as out of range. In some embodiments, validation may be based a range of values. In other embodiments, validation may be based on historical data and/or trend. For example, even if the blood pressure is with a valid range, but has increased too much since last measurement, an alert will be generated. In some implementations, validation may be based on a specific protocol, such as medication dosage. An alert and/or alarm may be generated indicating that an entered value is outside of a range, according to some embodiments of the present disclosure.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An emergency medical services (EMS) charting and treatment system comprising:
    a clinical device comprising a defibrillator and a patient monitor, the clinical device configured to monitor and provide treatment for a medical condition of a patient;
    at least one processor configured to execute a web-based smartphone EMS charting application to generate an electronic chart for an EMS encounter between one or more caregivers and the patient; and
    at least one memory comprising the web-based smartphone EMS charting application and the electronic chart;
    wherein the at least one processor is configured to:
        display, via an interactive user interface, a portion of the electronic chart for the EMS encounter, the displayed portion of the electronic chart comprising a plurality of displayed fields and a plurality of selectable tabs, each selectable tab representing a corresponding set of fields;
        receive first charting information from the one or more caregivers as voice data captured by a voice recognition interface, the first charting information comprising a name of a destination healthcare facility for the patient;
        identify at least one first displayed field of the electronic chart based on the voice data;
        populate the at least one first displayed field of the electronic chart stored locally in the at least one memory with the first charting information;
        transmit, via a networked connection, to a remote database, a query for second charting information that is stored in the remote database and that is based on the first charting information;
        receive the second charting information, wherein the second charting information comprises address information for the destination healthcare facility for the patient, and wherein the second charting information further comprises additional patient-specific information;
        automatically populate at least one second displayed field of the electronic chart with at least a portion of the second charting information;
        receive, via the interactive user interface, user input assigning a value to an encounter disposition field of the electronic chart;
        in response to receiving the user input, assign a default value to a third field of the electronic chart and disabling a particular one of the selectable tabs, wherein the particular selectable tab that is disabled represents a particular set of fields that are disabled based on the user input;
        display, via the interactive user interface, an update of the displayed portion of the electronic chart, wherein the update of the displayed portion of the electronic chart includes the first charting information and a first portion of the additional patient-specific information, but does not include a second portion of the additional patient-specific information;
        receive third charting information comprising identification information for the clinical device;
        receive fourth charting information comprising at least one of a patient age, a patient gender, a patient weight, a patient treatment history, a patient medical condition, or a patient medication;
        while the clinical device is being used to provide treatment for the patient, transmit at least a portion of the fourth charting information to the clinical device based on the third charting information, wherein the portion of the fourth charting information transmitted to the clinical device (a) is required by the clinical device to provide treatment for the patient, and (b) modifies operation of the clinical device to operate at treatment parameters based on the fourth charting information;
        receive a request for the electronic chart from the destination healthcare facility; and
        provide the electronic chart to the destination healthcare facility via a secure communications link.

2. The system of claim 1, wherein the interactive user interface is configured to prompt the one or more caregivers to provide the first charting information according to a template.

3. The system of claim 2, wherein the at least one processor is configured to customize the template based on previously received charting information.

4. The system of claim 1, wherein the interactive user interface is configured to prompt the one or more caregivers to provide fifth third charting information based on at least one of the first or the second charting information.

5. The system of claim 1, wherein the at least one processor is configured to automatically disable one or more of the displayed fields based on the first charting information.

6. The system of claim 1, further comprising a mobile computing device that comprises a third party interface system, wherein the at least one processor is configured to:
    provide at least a portion of at least one of the first or the second charting information to a third party user via the third party interface system; and
    receive input from the third party user,
    wherein the third party user comprises a healthcare provider.

7. The system of claim 1, wherein the at least one processor is configured to receive the first charting information during an examination of the patient by the one or more caregivers.

8. The system of claim 1, further comprising a mobile computing device that is configured to scan patient data and provide the scanned patient data to the at least one processor.

9. The system of claim 8, wherein the scanned patient data comprises driver's license information.

10. The system of claim 1, wherein the at least one processor is configured to:
    identify a database source of fifth charting information based on at least one of the first or the second charting information; and
    retrieve the fifth charting information from the database source.

11. The system of claim 10, wherein the fifth charting information comprises patient medications.

12. The system of claim 11, wherein the at least one of the first or the second charting information comprises a patient address and the database source comprises a pharmacy proximate to the patient address.

13. The system of claim 10, wherein the fifth-charting information comprises patient medical history information.

14. The system of claim 10, wherein the at least one processor is configured to communicate with the database source according to a health data exchange standard.

15. The system of claim 14, wherein the database source is part of a different organization than an organization with which the EMS charting and treatment system is associated.

16. The system of claim 1, wherein the at least one processor is configured to validate the first and the second charting information.

17. The system of claim 16, wherein the at least one processor is configured to validate the first and the second charting information based on a medical protocol.

18. The system of claim 1, wherein the at least one processor is configured to generate alerts at the interactive user interface based on one or more of (a) a rate of change of the additional patient-specific information, (b) the additional patient-specific information being outside of a predetermined range, or (c) the additional patient-specific information exceeding a predetermined rate of change since a previous data input.

19. The system of claim 1, further comprising a mobile computing device that is configured to communicate bidirectionally with the clinical device to send the portion of the fourth charting information to the clinical device and receive fifth charting information from the clinical device.

20. The system of claim 19, wherein the clinical device is configured to provide one or more of electrical shock therapy, respiration therapy, or drug therapy.

21. The system of claim 1, wherein the web-based smartphone EMS charting application is a web browser.

22. The system of claim 1, wherein the at least one processor is configured to adapt the interactive user interface based on a form factor of a mobile computing device on which the web-based smartphone EMS charting application is executing.

23. The system of claim 1, wherein the interactive user interface comprises a touchscreen interface.

24. The system of claim 1, wherein the additional patient-specific information comprises at least one of a patient name or a patient allergy.

25. The system of claim 1, wherein the additional patient-specific information includes a location of the patient.

* * * * *